(12) United States Patent
Bodhuri et al.

(10) Patent No.: US 8,435,989 B2
(45) Date of Patent: May 7, 2013

(54) PROCESSES FOR THE PREPARATION OF RIVAROXABAN AND INTERMEDIATES THEREOF

(71) Applicant: Apotex Pharmachem Inc., Brantford (CA)

(72) Inventors: Prabhudas Bodhuri, Brantford (CA); Gamini Weeratunga, Ancaster (CA)

( * ) Notice: Subject to any disclaimer, the term of this patent is extended or adjusted under 35 U.S.C. 154(b) by 0 days.

(21) Appl. No.: 13/674,677

(22) Filed: Nov. 12, 2012

(65) Prior Publication Data

US 2013/0072680 A1 Mar. 21, 2013

Related U.S. Application Data

(60) Continuation-in-part of application No. 12/431,272, filed on Apr. 28, 2009, now Pat. No. 7,816,355, and a continuation-in-part of application No. 12/767,436, filed on Apr. 26, 2010, now Pat. No. 8,101,609, and a division of application No. 12/906,907, filed on Oct. 18, 2010, now Pat. No. 8,309,547.

(51) Int. Cl.
*A61K 31/5377* (2006.01)
*C07D 413/14* (2006.01)

(52) U.S. Cl.
USPC ........................................ 514/236.8; 544/137

(58) Field of Classification Search ............... 514/236.8; 544/137

See application file for complete search history.

(56) References Cited

U.S. PATENT DOCUMENTS 7,351,823 B2 * 4/2008 Berwe et al. .................. 544/137

* cited by examiner

*Primary Examiner* — Kristin Bianchi

(57) ABSTRACT

Provided are process for the preparation of (R)- and/or (S)-Rivaroxaban, and compounds which are intermediate compounds used in the processes for the preparation of (R)- and/or (S)-Rivaroxaban.

20 Claims, No Drawings

PROCESSES FOR THE PREPARATION OF RIVAROXABAN AND INTERMEDIATES THEREOF

This application is a continuation-in-part of U.S. application Ser. No. 12/431,272, filed on Apr. 28, 2009, now U.S. Pat. No. 7,816,355, a continuation-in-part of U.S. application Ser. No. 12/767,436, filed on Apr. 26, 2010, now U.S. Pat. No. 8,101,609, and a division of U.S. application Ser. No. 12/906,907, filed on Oct. 18, 2010, now U.S. Pat. No. 8,309,547.

TECHNICAL FIELD

The present invention relates to the field of synthesis of organic compounds and in particular to methods for the synthesis of Rivaroxaban and intermediates thereof.

BACKGROUND

Rivaroxaban (1) (5-chloro-N-{[(5S)-2-oxo-3-[4-(3-oxo-morpholin-4-yl)phenyl]oxazolidin-5-yl}methyl]thiophene-2-carboxamide) is a low molecular weight, orally administrable anticoagulant drug. The pharmaceutical directly inhibits the active form of serine protease Factor Xa (FXa). Rivaroxaban can be used for the prevention and treatment of various thromboembolic diseases, in particular of deep vein thrombosis (DVT), pulmonary embolism (PE), myocardial infraction, angina pectoris, reocclusions and restenoses after angioplasty or aortocoronary bypass, cerebral stroke, transitory ischemic attacks, and peripheral arterial occlusive diseases.

Rivaroxaban is disclosed in WO 01/47919 and has the following structure:

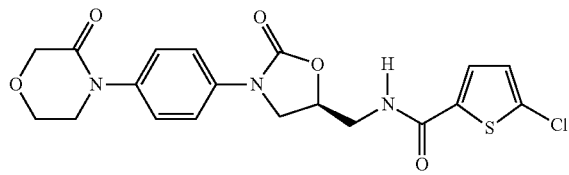

(1)

US 2007/0149522 relates to a method for producing 5-chloro-N-{(5S)-2-oxo-3-[4-(3-oxo-4-morpholinyl)phenyl]-1,3-oxazolidin-5-yl}-methyl)thiophene-2-carboxamide starting from 5-chlorothiophene-2-carbonylchloride and (2S)-3-amino-propane-1,2-diol and 4-(4-aminophenyl)-3-morpholinone.

U.S. Pat. No. 7,598,378 relates to a process for preparing 4-(4-aminophenyl)-3-morpholinone by reacting 4-(4-nitrophenyl)-3-morpholinone with hydrogen in the presence of a hydrogenation catalyst, characterized in that the reaction is effected in an aliphatic alcohol.

U.S. Pat. No. 7,351,823 relates to a process for preparing 5-chloro-N-({(5S)-2-oxo-3-[4-(3-oxo-4-morpholinyl)phenyl]-1,3-oxazolidin-5-yl}methyl)-2-thiophenecarboxamide starting from 2-[(2S)-2-oxiranylmethyl]-1H-isoindole-1,3-(2H)-dione, 4-(4-aminophenyl)-3-morpholinone and 5-chlorothiophene-2-carbonyl chloride.

WO 2009/023233 relates to novel compounds that are substituted oxazolidinones derivatives and pharmaceutically acceptable salts thereof. More specifically, this invention relates to novel oxazolidinone compounds that are derivatives of Rivaroxaban. The invention also provides pyrogen-free compositions comprising one or more compounds of the invention and a carrier, along with the use of the disclosed compounds and compositions in methods of treating diseases and conditions that are beneficially treated by administering a selective inhibitor of factor Xa, such as Rivaroxaban.

SUMMARY

The present invention is directed to methods of preparation of S and/or R Rivaroxaban, various intermediates useful in the preparation of S and/or R Rivaroxaban and methods of preparation of such intermediates.

In illustrative embodiments of the present invention, there is provided a compound of Formula 13:

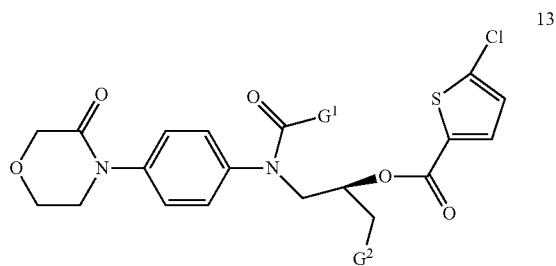

13 wherein $G^1$ is $OR^1$, $NR^2R^3$ or $CQ^3$; $R^1$ is alkyl, substituted alkyl, aryl, substituted aryl, arylalkyl or substituted arylalkyl; $R^2$ and $R^3$ are either (a) two independent groups or (b) together form a single ring group with the N to which they are bonded; $R^2$ and $R^3$, when independent groups, are independently selected from the group consisting of: H, alkyl, substituted alkyl, aryl, substituted aryl, arylalkyl and substituted arylalkyl; $R^2$ and $R^3$, when together form a single ring group with the N to which they are bonded, area heteroaryl ring; Q is halogen; and $G^2$ is a primary amine precursor.

In illustrative embodiments of the present invention there is provided a compound described herein wherein $G^1$ is $OR^1$ and $G^2$ is an azide or $NR^{2'}R^{3'}$, wherein $R^{2'}$ and $R^{3'}$ are either two independent groups or together form a single ring group with the N to which they are bonded; $R^{2'}$ and $R^{3'}$, when independent groups, are independently selected from the group consisting of: hydrogen and a suitable amine protecting group, provided that both $R^{2'}$ and $R^{3'}$ are not both hydrogen; $R^{2'}$ and $R^{3'}$, when together, form a single ring group with the N to which they are bonded, area heterocyclic ring, a substituted heterocyclic ring, phthalimide or saccharin.

In illustrative embodiments of the present invention there is provided a compound described herein wherein $G^1$ is $OR^1$ and $G^2$ is an azide, heterocyclic or substituted heterocyclic ring.

In illustrative embodiments of the present invention there is provided a compound described herein wherein $R^1$ is an alkyl and $G^2$ is a heterocyclic ring or a substituted heterocyclic ring.

In illustrative embodiments of the present invention there is provided a compound described herein wherein $G^1$ is methoxy and $G^2$ is phthalimide.

In illustrative embodiments of the present invention there is provided a compound of Formula 14:

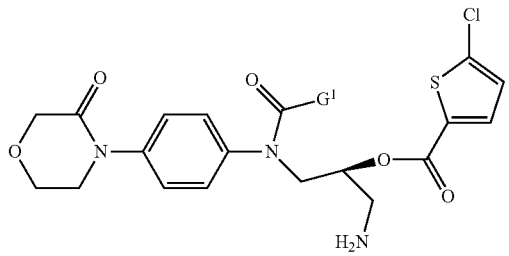

14

$G^1$ is $OR^1$, $NR^2R^3$ or $CQ_3$; $R^1$ is alkyl, substituted alkyl, aryl, substituted aryl, arylalkyl or substituted arylalkyl; $R^2$ and $R^3$ are either (a) two independent groups or (b) together form a single ring group with the N to which they are bonded; $R^2$ and $R^3$, when independent groups, are independently selected from the group consisting of: H, alkyl, substituted alkyl, aryl, substituted aryl, arylalkyl and substituted arylalkyl; $R^2$ and $R^3$, when together form a single ring group with the N to which they are bonded, are a heteroaryl ring; and Q is halogen.

In illustrative embodiments of the present invention there is provided a compound of Formula 14a:

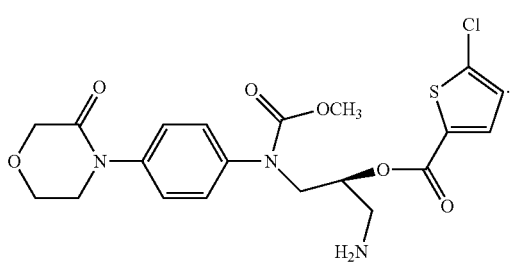

14a

In illustrative embodiments of the present invention there is provided a compound of Formula 15:

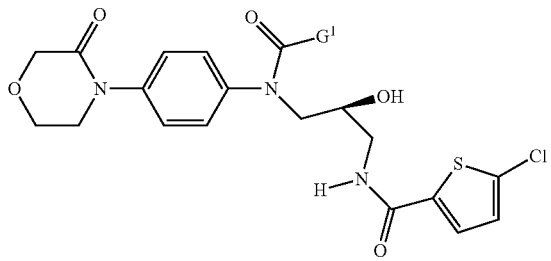

15 wherein $G^1$ is $OR^1$, $NR^2R^3$ or $CO_3$; $R^1$ is alkyl, substituted alkyl, aryl, substituted aryl, arylalkyl or substituted arylalkyl; $R^2$ and $R^3$ are either (a) two independent groups or (b) together form a single ring group with the N to which they are bonded; $R^2$ and $R^3$, when independent groups, are independently selected from the group consisting of: H, alkyl, substituted alkyl, aryl, substituted aryl, arylalkyl and substituted arylalkyl; $R^2$ and $R^3$, when together form a single ring group with the N to which they are bonded, are a heteroaryl ring; and Q is halogen.

In illustrative embodiments of the present invention there is provided a compound of Formula 15a:

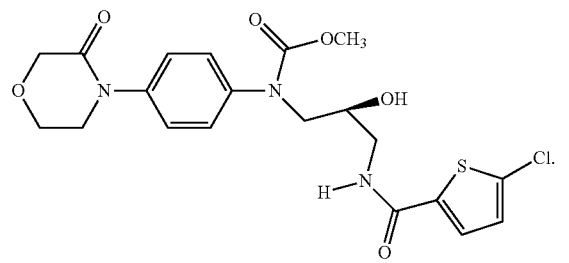

15a

In illustrative embodiments of the present invention there is provided a compound of Formula 11:

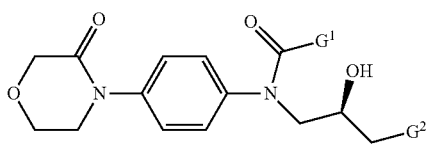

11 wherein $G^1$ is $OR^1$, $NR^2R^3$ or $CQ_3$; $R^1$ is alkyl, substituted alkyl, aryl, substituted aryl, arylalkyl or substituted arylalkyl; $R^2$ and $R^3$ are either (a) two independent groups or (b) together form a single ring group with the N to which they are bonded; $R^2$ and $R^3$, when independent groups, are independently selected from the group consisting of: H, alkyl, substituted alkyl, aryl, substituted aryl, arylalkyl and substituted arylalkyl; $R^2$ and $R^3$, when together form a single ring group with the N to which they are bonded, are a heteroaryl ring; Q is halogen; and $G^2$ is a primary amine precursor.

In illustrative embodiments of the present invention there is provided a compound described herein wherein $G^1$ is $OR^1$ and $G^2$ is an azide, heterocyclic or substituted heterocyclic ring.

In illustrative embodiments of the present invention there is provided a compound described herein wherein $R^1$ is alkyl and $G^2$ is a heterocyclic or substituted heterocyclic ring.

In illustrative embodiments of the present invention there is provided a compound described herein wherein $R^1$ is methyl and $G^2$ is phthalimide.

In illustrative embodiments of the present invention, there is provided a process for the preparation of (S)- or (R)-Rivaroxaban comprising reacting a primary amine formation agent with a compound of Formula 13':

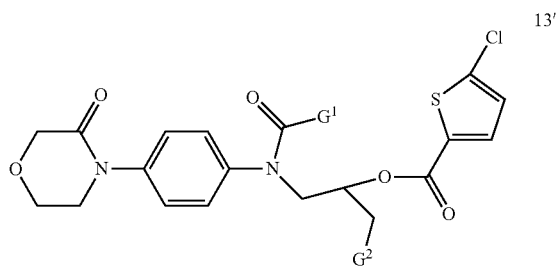

13' wherein $G^1$ is $OR^1$, $NR_2R_3$ or $CO_3$; $R^1$ is alkyl, substituted alkyl, aryl, substituted aryl, arylalkyl or substituted arylalkyl; $R^2$ and $R^3$ are either (a) two independent groups or (b) together form a single ring group with the N to which they are bonded; $R^2$ and $R^3$, when independent groups, are independently selected from the group consisting of: H, alkyl, substituted alkyl, aryl, substituted aryl, arylalkyl and substituted arylalkyl; $R^2$ and $R^3$, when together form a single ring group with the N to which they are bonded, are a heteroaryl ring; Q is halogen; and $G^2$ is a primary amine precursor.

In illustrative embodiments of the present invention there is provided a process described herein wherein the suitable primary amine formation agent is selected from the group consisting of: hydrogen, hydride based reducing agents, metal catalyzed reducing agents, acids and $R—NR^4R^5$ wherein R is hydrogen, —OH, alkyl, substituted alkyl, aryl, substituted aryl, arylalkyl or substituted arylalkyl; $R^4$ and $R^5$ are either two independent groups or together form a single ring group with the N to which they are bonded; $R^4$ and $R^5$, when independent groups, are independently selected from the group consisting of: H, alkyl, substituted alkyl, aryl, substituted aryl, arylalkyl, substituted arylalkyl, amine and substituted amino; and $R^4$ and $R^5$, when together form a single ring group with the N to which they are bonded, are a heteroaryl ring.

In illustrative embodiments of the present invention there is provided a process described herein wherein reacting the compound of Formula 13' with the suitable primary amine formation agent occurs in the presence of a first base selected from the group consisting of: metal hydroxides, carbonates, phosphates, tertiary amines, aryl amines, and mixtures thereof.

In illustrative embodiments of the present invention there is provided a process described herein wherein the first base is selected from the group consisting of: sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline, N,N-diethylaniline, pyridine, n-butyl lithium, lithium diisopropylamide (LDA), lithium hexamethyldisilazide (LiHMDS), sodium hexamethyldisilazide (NaHMDS), potassium hexamethyldisilazide (KHMDS), sodium hydride (NaH), potassium hydride (KH), potassium tert-butoxide and mixtures thereof.

In illustrative embodiments of the present invention there is provided a process described herein wherein reacting the compound of Formula 13' with the suitable primary amine formation agent occurs in a first solvent selected from the group consisting of: alcohols, alkyl ethers, aryl ethers, arylalkyl ethers, alkyl esters, alkyl ketones, aromatic hydrocarbons, aliphatic hydrocarbons, nitriles, N,N-dialkylamides, sulfoxides and sulfones, halogenated hydrocarbons, and mixtures thereof.

In illustrative embodiments of the present invention there is provided a process described herein wherein the first solvent is selected from the group consisting of: methanol, ethanol, propanol, isopropanol, butanol, tetrahydrofuran, dioxane, diethyl ether, methyl t-butyl ether, diisopropyl ether, butyl ether, diphenyl ether, methylphenyl ether, ethyl acetate, isopropyl acetate, acetone, methyl ethyl ketone, methyl isobutyl ketone, toluene, xylenes, hexanes, heptanes, acetonitrile, propionitrile, butyronitrile, benzonitrile, N,N-dimethylformamide, N,N-dimethylacetamide, N-methyl-2-pyrrolidinone, dimethyl sulfoxide, sulfolane, dichloromethane, dichloroethane, and mixtures thereof.

In illustrative embodiments of the present invention there is provided a process described herein further comprising reacting a compound of Formula 11':

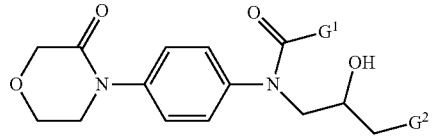

11' with a compound of Formula 12:

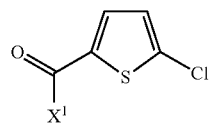

12 thereby forming the compound of Formula 13' wherein $G^1$ is $OR^1$, $NR^2R^3$ or $CO_3$; $R^1$ is alkyl, substituted alkyl, aryl, substituted aryl, arylalkyl or substituted arylalkyl; $R^2$ and $R^3$ are either (a) two independent groups or (b) together form a single ring group with the N to which they are bonded; $R^2$ and $R^3$, when independent groups, are independently selected from the group consisting of: H, alkyl, substituted alkyl, aryl, substituted aryl, arylalkyl and substituted arylalkyl; $R^2$ and $R^3$, when together form a single ring group with the N to which they are bonded, are a heteroaryl ring; Q is halogen; $G^2$ is a primary amine precursor; and $X^1$ is a leaving group selected from the group consisting of halogen, sulfonyloxy, imidazole, ester, $C_1$-$C_4$ alkoxy, substituted $C_1$-$C_4$ alkoxy, trihalomethoxy. N-hydroxysuccinimide, p-nitrophenol, N-hydroxyphthalimide, and N-hydroxybenzotriazole.

In illustrative embodiments of the present invention there is provided a process described herein wherein reacting the compound of Formula 11' with the compound of Formula 12 occurs in the presence of a second base selected from the group consisting of: metal hydroxides, carbonates, phosphates, tertiary amines, aryl amines, and mixtures thereof.

In illustrative embodiments of the present invention there is provided a process described herein wherein the second base is selected from the group consisting of: sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, diisopropylethylamine, N,N-dimethylaniline, N,N-diethylaniline, pyridine, 4-(dimethylamino)pyridine, 1,8-diazabicyclo[5.4.0]undec-7-ene (DBU), 1,5-diazabicyclo[4.3.0]non-5-ene (DBN), n-butyl lithium, lithium diisopropylamide (LDA), lithium hexamethyldisilazide (LiHMDS), sodium hexamethyldisilazide (NaHMDS), potassium hexamethyldisilazide (KHMDS), sodium hydride (NaH), potassium hydride (KH), potassium tert-butoxide and mixtures thereof.

In illustrative embodiments of the present invention there is provided a process described herein wherein reacting the compound of Formula 11' with the compound of Formula 12 occurs in a second solvent selected from the group consisting of: alkyl ethers, aryl ethers, arylalkyl ethers, alkyl esters, alkyl ketones, aromatic hydrocarbons, aliphatic hydrocarbons, nitriles, N,N-dialkylamides, sulfoxides, sulfones, halogenated hydrocarbons, and mixtures thereof.

In illustrative embodiments of the present invention there is provided a process described herein wherein the second solvent is selected from the group consisting of: tetrahydrofuran, dioxane, diethyl ether, methyl t-butyl ether, diisopropyl ether, butyl ether, diphenyl ether, methylphenyl ether, ethyl acetate, isopropyl acetate, acetone, methyl ethyl ketone, methyl isobutyl ketone, toluene, xylenes, hexanes, heptanes, acetonitrile, propionitrile, butyronitrile, benzonitrile, N,N-dimethylformamide, N,N-dimethylacetamide, N-methyl-2-pyrrolidinone, dimethyl sulfoxide, sulfolane, dichloromethane, dichloroethane, and mixtures thereof.

In illustrative embodiments of the present invention there is provided a process described herein further comprising reacting a compound of Formula 9:

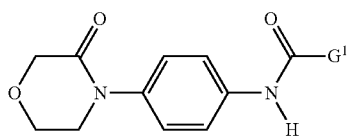

with a compound of Formula 10':

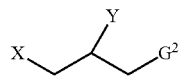

thereby forming the compound of Formula 11' wherein $G^1$ is $OR^1$, $NR^2R^3$ or $CQ_3$; $R^1$ is alkyl, substituted alkyl, aryl, substituted aryl, arylalkyl or substituted arylalkyl; $R^2$ and $R^3$ are either (a) two independent groups or (b) together form a single ring group with the N to which they are bonded; $R^2$ and $R^3$, when independent groups, are independently selected from the group consisting of: H, alkyl, substituted alkyl, aryl, substituted aryl, arylalkyl and substituted arylalkyl; $R^2$ and $R^3$, when together form a single ring group with the N to which they are bonded, are a heteroaryl ring; Q is halogen; X and Y are either i) separate groups or ii) together form a single ring group with the two carbons to which they are bonded; and when: i) X and Y are separate groups, X is a halogen and Y is —OH; or ii) X and Y together form a single ring group with the two carbons to which they are bonded, they are an oxygen atom; and $G^2$ is a primary amine precursor.

In illustrative embodiments of the present invention there is provided a process described herein wherein reacting the compound of Formula 9 with the compound of Formula 10' occurs in the presence of a third base selected from the group consisting of: metal hydroxides, carbonates, phosphates, tertiary amines, and aryl amines.

In illustrative embodiments of the present invention there is provided a process described herein wherein the third base is selected from the group consisting of: sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline, N,N-diethylaniline, pyridine, n-butyl lithium, lithium diisopropylamide (LDA), lithium hexamethyldisilazide (LiHMDS), sodium hexamethyldisilazide (NaHMDS), potassium hexamethyldisilazide (KHMDS), sodium hydride (NaH), potassium hydride (KH), potassium tert-butoxide, and mixtures thereof.

In illustrative embodiments of the present invention there is provided a process described herein wherein reacting the compound of Formula 9 with the compound of Formula 10' occurs in a third solvent selected from the group consisting of: alcohols, alkyl ethers, aryl ethers, arylalkyl ethers, alkyl esters, alkyl ketones, aromatic hydrocarbons, aliphatic hydrocarbons, nitriles. N,N-dialkylamides, sulfoxides, sulfones, halogenated hydrocarbons, and mixtures thereof.

In illustrative embodiments of the present invention there is provided a process described herein wherein the third solvent is selected from the group consisting of: methanol, ethanol, n-propanol, isopropanol, butanol, tetrahydrofuran, dioxane, diethyl ether, methyl t-butyl ether, diisopropyl ether, butyl ether, diphenyl ether, methylphenyl ether, ethyl acetate, isopropyl acetate, acetone, methyl ethyl ketone, methyl isobutyl ketone, toluene, xylenes, hexanes, heptanes, acetonitrile, propionitrile, butyronitrile, benzonitrile. N,N-dimethylformamide, N,N-dimethylacetamide, N-methyl-2-pyrrolidinone, dimethyl sulfoxide sulfolane, dichloromethane, dichloroethane, and mixtures thereof.

In illustrative embodiments of the present invention there is provided a process described herein further comprising reacting a compound of Formula 7':

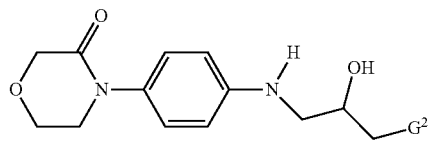

with a compound of Formula 8:

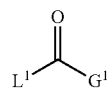

thereby forming the compound of Formula 11' wherein $L^1$ is a leaving group selected from the group consisting of: halogen, imidazole, ester, $C_1$-$C_4$ alkoxy, trihalomethoxy, N-hydroxysuccinimide, p-nitrophenol, N-hydroxyphthalimide, and N-hydroxybenzotriazole; $G^1$ is $OR^1$, $NR^2R^3$ or $CQ_3$; $R^1$ is alkyl, substituted alkyl, aryl, substituted aryl, arylalkyl or substituted arylalkyl; $R^2$ and $R^3$ are either (a) two independent groups or (b) together form a single ring group with the N to which they are bonded; $R^2$ and $R^3$, when independent groups, are independently selected from the group consisting of: H, alkyl, substituted alkyl, aryl, substituted aryl, arylalkyl and substituted arylalkyl; $R^2$ and $R^3$, when together form a single ring group with the N to which they are bonded, are a heteroaryl ring; Q is halogen; and $G^2$ is a primary amine precursor.

In illustrative embodiments of the present invention there is provided a process described herein wherein reacting the compound of Formula 7' with the compound of Formula 8 occurs in the presence of a fourth base selected from the group consisting of: metal hydroxides, carbonates, phosphates, tertiary amines, aryl amines, and mixtures thereof.

In illustrative embodiments of the present invention there is provided a process described herein wherein the fourth base is selected from the group consisting of: sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, diisopropylethylamine, N,N-dimethylaniline, N,N-diethylaniline, pyridine, and mixtures thereof.

In illustrative embodiments of the present invention there is provided a process described herein wherein reacting the compound of Formula 7' with the compound of Formula 8 occurs in the presence of a fourth solvent selected from the group consisting of: water, alcohols, alkyl ethers, aryl ethers, arylalkyl ethers, alkyl esters, alkyl ketones, aromatic hydrocarbons, aliphatic hydrocarbons, nitriles, N,N-dialkylamides, sulfoxides, sulfones, halogenated hydrocarbons, and mixtures thereof.

In illustrative embodiments of the present invention there is provided a process described herein wherein the fourth solvent is selected from the group consisting of: methanol, ethanol, n-propanol, isopropanol, butanol, tetrahydrofuran, dioxane, diethyl ether, methyl t-butyl ether, diisopropyl ether, butyl ether, diphenyl ether, methylphenyl ether, ethyl acetate, isopropyl acetate, acetone, methyl ethyl ketone, methyl isobutyl ketone, toluene, xylenes, hexanes, heptanes, acetonitrile, propionitrile, butyronitrile, benzonitrile, N,N-dimethylformamide, N,N-dimethylacetamide, N-methyl-2-pyrrolidinone, dimethyl sulfoxide, sulfolane, dichloromethane dichloroethane, and mixtures thereof.

In illustrative embodiments of the present invention there is provided a process described herein further comprising, reacting a compound of Formula 2:

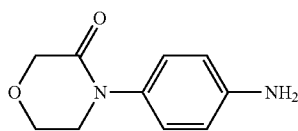

2 with a compound of Formula 8:

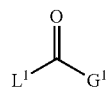

8 thereby forming the compound of Formula 9 wherein $L^1$ is a leaving group selected from the group consisting of: halogen, imidazole, ester, $C_1$-$C_4$ alkoxy, trihalomethoxy, N-hydroxysuccinimide, p-nitrophenol, N-hydroxyphthalimide, and N-hydroxybenzotriazole; $G^1$ is $OR^1$, $NR^2R^3$ or $CO_3$; $R^1$ is alkyl, substituted alkyl, aryl, substituted aryl, arylalkyl or substituted arylalkyl; $R^2$ and $R^3$ are either (a) two independent groups or (b) together form a single ring group with the N to which they are bonded; $R^2$ and $R^3$, when independent groups, are independently selected from the group consisting of: H, alkyl, substituted alkyl, aryl, substituted aryl, arylalkyl and substituted arylalkyl; $R^2$ and $R^3$, when together form a single ring group with the N to which they are bonded, are a heteroaryl ring; and Q is halogen.

In illustrative embodiments of the present invention there is provided a process described herein wherein reacting the compound of Formula 2 with the compound of Formula 8 occurs in the presence of an eighth base selected from the group consisting of: metal hydroxides, carbonates, phosphates, tertiary amines, aryl amines, and mixtures thereof.

In illustrative embodiments of the present invention there is provided a process described herein wherein the eighth base is selected from the group consisting of: sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, diisopropylethylamine, N,N-dimethylaniline, N,N-diethylaniline, pyridine, and mixtures thereof.

In illustrative embodiments of the present invention there is provided a process described herein wherein reacting the compound of Formula 2 with the compound of Formula 8 occurs in the presence of an eighth solvent selected from the group consisting of: water, alcohols, alkyl ethers, aryl ethers, arylalkyl ethers, alkyl esters, alkyl ketones, aromatic hydrocarbons, aliphatic hydrocarbons, nitriles, N,N-dialkylamides, sulfoxides, sulfones, halogenated hydrocarbons, and mixtures thereof.

In illustrative embodiments of the present invention there is provided a process described herein wherein the eighth solvent is selected from the group consisting of: methanol, ethanol, n-propanol, isopropanol, butanol, tetrahydrofuran, dioxane, diethyl ether, methyl t-butyl ether, diisopropyl ether, butyl ether, diphenyl ether, methylphenyl ether, ethyl acetate, isopropyl acetate, acetone, methyl ethyl ketone, methyl isobutyl ketone, toluene, xylenes, hexanes, heptanes, acetonitrile, propionitrile, butyronitrile, benzonitrile, N,N-dimethylformamide, N,N-dimethylacetamide, N-methyl-2-pyrrolidinone, dimethyl sulfoxide, sulfolane, dichloromethane dichloroethane, and mixtures thereof.

In illustrative embodiments of the present invention there is provided a process described herein further comprising reacting a compound of Formula 2:

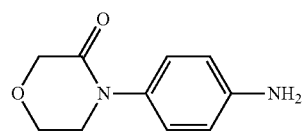

2 with a compound of Formula 10':

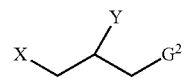

10' thereby forming the compound of Formula 7' wherein X and Y are either i) separate groups or ii) together form a single ring group with the two carbons to which they are bonded; and when: i) X and Y are separate groups, X is a halogen and Y is —OH; or ii) X and Y together form a single ring group with the two carbons to which they are bonded, they are an oxygen atom; and $G^2$ is a primary amine precursor.

In illustrative embodiments of the present invention there is provided a process described herein wherein reacting the compound of Formula 2 with the compound of Formula 10' occurs in the presence of a ninth base selected from the group consisting of: metal hydroxides, carbonates, phosphates, tertiary amines, aryl amines, and mixtures thereof.

In illustrative embodiments of the present invention there is provided a process described herein wherein the ninth base is selected from the group consisting of: sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline, N,N-diethylaniline, pyridine, and mixtures thereof.

In illustrative embodiments of the present invention there is provided a process described herein wherein reacting the compound of Formula 2 with the compound of Formula 10' occurs in a ninth solvent selected from the group consisting of: water, alcohols, alkyl ethers, aryl ethers, arylalkyl ethers, alkyl esters, alkyl ketones, aromatic hydrocarbons, aliphatic hydrocarbons, nitriles. N,N-dialkylamides, sulfoxides, sulfones, halogenated hydrocarbons, and mixtures thereof.

In illustrative embodiments of the present invention there is provided a process described herein wherein the ninth solvent is selected from the group consisting of: methanol, ethanol, n-propanol, isopropanol, butanol, tetrahydrofuran, dioxane, diethyl ether, methyl t-butyl ether, diisopropyl ether, butyl ether, diphenyl ether, methylphenyl ether, ethyl acetate, isopropyl acetate, acetone, methyl ethyl ketone, methyl isobutyl ketone, toluene, xylenes, hexanes, heptanes, acetonitrile, propionitrile, butyronitrile, benzonitrile, N,N-dimethylformamide, N,N-dimethylacetamide, N-methyl-2-pyrrolidinone, dimethyl sulfoxide sulfolane, dichloromethane, dichloroethane, and mixtures thereof.

In illustrative embodiments of the present invention there is provided a process described herein further comprising reacting either: i) a compound of Formula 4':

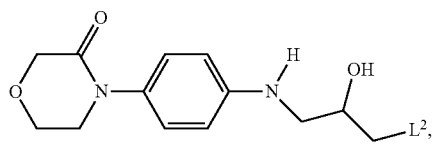

4' or ii) a compound of Formula 6':

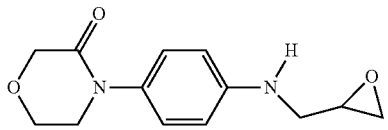

6' with a compound of Formula 5:

5 thereby forming the compound of Formula 7' wherein $L^2$ is a halogen or sulfonyloxy group; M is H or a metal selected from the group consisting of Li, Na and K; and $G^2$ is a primary amine precursor.

In illustrative embodiments of the present invention there is provided a process described herein wherein the compound of Formula 4' is reacted with the compound of Formula 5.

In illustrative embodiments of the present invention there is provided a process described herein wherein reacting the compound of Formula 4' or the compound of Formula 6' with the compound of Formula 5 occurs in the presence of a fifth base selected from the group consisting of: metal hydroxides, carbonates, phosphates, tertiary amines, aryl amines, and mixtures thereof.

In illustrative embodiments of the present invention there is provided a process described herein wherein the fifth base is selected from the group consisting of: sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline. N,N-diethylaniline, pyridine, n-butyl lithium, lithium diisopropylamide (LDA), lithium hexamethyldisilazide (LiHMDS), sodium hexamethyldisilazide (NaHMDS), potassium hexamethyldisilazide (KHMDS), sodium hydride (NaH), potassium hydride (KH), potassium tert-butoxide, and mixtures thereof.

In illustrative embodiments of the present invention there is provided a process described herein wherein reacting the compound of Formula 4' or the compound of Formula 6' with the compound of Formula 5 occurs in the presence of a fifth solvent selected from the group consisting of: water, alcohols, alkyl ethers, aryl ethers, arylalkyl ethers, alkyl esters, alkyl ketones, aromatic hydrocarbons, aliphatic hydrocarbons, nitriles. N,N-dialkylamides, sulfoxides, sulfones, halogenated hydrocarbons, and mixtures thereof.

In illustrative embodiments of the present invention there is provided a process described herein wherein the fifth solvent is selected from the group consisting of: methanol, ethanol, n-propanol, isopropanol, butanol, tetrahydrofuran, dioxane, diethyl ether, methyl t-butyl ether, diisopropyl ether, butyl ether, diphenyl ether, methylphenyl ether, ethyl acetate, isopropyl acetate, acetone, methyl ethyl ketone, methyl isobutyl ketone, toluene, xylenes, hexanes, heptanes, acetonitrile, propionitrile, butyronitrile, benzonitrile. N,N-dimethylformamide, N,N-dimethylacetamide. N-methyl-2-pyrrolidinone, dimethyl sulfoxide, sulfolane, dichloromethane, dichloroethane, and mixtures thereof.

In illustrative embodiments of the present invention there is provided a process described herein further comprising reacting a compound of Formula 2:

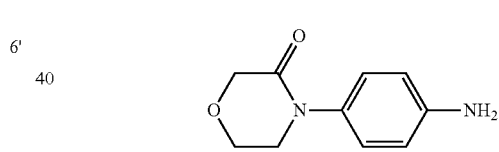

2 with a compound of Formula 3':

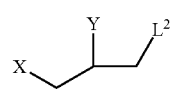

3' thereby forming the compound of Formula 4' wherein X and Y are either i) separate groups or ii) together form a single ring group with the two carbons to which they are bonded; and when: i) X and Y are separate groups, X is a halogen and Y is —OH; or ii) X and Y together form a single ring group with the two carbons to which they are bonded, they are an oxygen atom; and $L^2$ is a halogen or sulfonyloxy group.

In illustrative embodiments of the present invention there is provided a process described herein wherein reacting the compound of Formula 2 with the compound of Formula 3' occurs in the presence of a seventh base selected from the group consisting of: metal hydroxides, carbonates, phosphates, tertiary amines, aryl amines, and mixtures thereof.

In illustrative embodiments of the present invention there is provided a process described herein wherein the seventh base is selected from the group consisting of: sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline, N,N-diethylaniline, pyridine, and mixtures thereof.

In illustrative embodiments of the present invention there is provided a process described herein wherein reacting the compound of Formula 2 with the compound of Formula 3' occurs in the presence of a seventh solvent selected from the group consisting of: water, alcohols, alkyl ethers, aryl ethers, arylalkyl ethers, alkyl esters, alkyl ketones, aromatic hydrocarbons, aliphatic hydrocarbons, nitriles. N,N-dialkylamides, sulfoxides, sulfones, halogenated hydrocarbons, and mixtures thereof.

In illustrative embodiments of the present invention there is provided a process described herein wherein the seventh solvent is selected from the group consisting of: methanol, ethanol, n-propanol, isopropanol, butanol, tetrahydrofuran, dioxane, diethyl ether, methyl t-butyl ether, diisopropyl ether, butyl ether, diphenyl ether, methylphenyl ether, ethyl acetate, isopropyl acetate, acetone, methyl ethyl ketone, methyl isobutyl ketone, toluene, xylenes, hexanes, heptanes, acetonitrile, propionitrile, butyronitrile, benzonitrile. N,N-dimethylformamide, N,N-dimethylacetamide, N-methyl-2-pyrrolidinone, dimethyl sulfoxide, sulfolane, dichloromethane, dichloroethane, and mixtures thereof.

In illustrative embodiments of the present invention there is provided a process described herein wherein the compound of Formula 6' is reacted with the compound of Formula 5.

In illustrative embodiments of the present invention there is provided a process described herein further comprising reacting a compound of Formula 4':

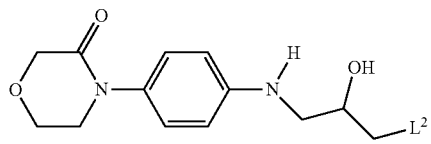

with a sixth base selected from the group consisting of: metal hydroxides, carbonates, phosphates, tertiary amines, aryl amines, and mixtures thereof, thereby forming the compound of Formula 6' wherein $L^2$ is a halogen or sulfonyloxy group.

In illustrative embodiments of the present invention there is provided a process described herein wherein the sixth base is selected from the group consisting of: sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline, N,N-diethylaniline, pyridine, and mixtures thereof.

In illustrative embodiments of the present invention there is provided a process described herein wherein reacting the compound of Formula 4' with the sixth base occurs in the presence of a sixth solvent selected from the group consisting of: water, alcohols, alkyl ethers, aryl ethers, arylalkyl ethers, alkyl esters, alkyl ketones, aromatic hydrocarbons, aliphatic hydrocarbons, nitriles, N,N-dialkylamides, sulfoxides, sulfones, halogenated hydrocarbons, and mixtures thereof.

In illustrative embodiments of the present invention there is provided a process described herein wherein the sixth solvent is selected from the group consisting of: methanol, ethanol, n-propanol, isopropanol, butanol, tetrahydrofuran, dioxane, diethyl ether, methyl t-butyl ether, diisopropyl ether, butyl ether, diphenyl ether, methylphenyl ether, ethyl acetate, isopropyl acetate, acetone, methyl ethyl ketone, methyl isobutyl ketone, toluene, xylenes, hexanes, heptanes, acetonitrile, propionitrile, butyronitrile, benzonitrile, N,N-dimethylformamide, N,N-dimethylacetamide, N-methyl-2-pyrrolidinone, dimethyl sulfoxide, sulfolane, dichloromethane, dichloroethane, and mixtures thereof.

In illustrative embodiments of the present invention there is provided a process described herein wherein $G^1$ is $OR^1$ and $G^2$ is an azide or $NR^{2'}R^{3'}$, wherein $R^{2'}$ and $R^{3'}$ are either two independent groups or together form a single ring group with the N to which they are bonded; $R^{2'}$ and $R^{3'}$, when independent groups, are independently selected from the group consisting of: hydrogen and a suitable amine protecting group, provided that both $R^{2'}$ and $R^{3'}$ are not both hydrogen; $R^{2'}$ and $R^{3'}$, when together, form a single ring group with the N to which they are bonded, area heterocyclic ring, a substituted heterocyclic ring, phthalimide or saccharin.

In illustrative embodiments of the present invention there is provided a process described herein wherein $G^1$ is $OR^1$ and $G^2$ is an azide, heterocyclic or substituted heterocyclic ring.

In illustrative embodiments of the present invention there is provided a process described herein wherein $R^1$ is an alkyl and $G^2$ is a heterocyclic ring or a substituted heterocyclic ring.

In illustrative embodiments of the present invention there is provided a process described herein wherein $G^1$ is methoxy and $G^2$ is phthalimide.

In illustrative embodiments of the present invention there is provided a process described herein wherein $G^1$ is $OR^1$ and $G^2$ is an azide, heterocyclic or substituted heterocyclic ring.

In illustrative embodiments of the present invention there is provided a process described herein wherein $R^1$ is alkyl and $G^2$ is a heterocyclic or substituted heterocyclic ring.

In illustrative embodiments of the present invention there is provided a process described herein wherein $R^1$ is methyl and $G^2$ is phthalimide.

In illustrative embodiments of the present invention there is provided a process described herein wherein $X^1$ is a sulfonyloxy group.

In illustrative embodiments of the present invention there is provided a process described herein wherein $X^1$ is a toluenesulfonyloxy, methanesulfonyloxy or trifluoromethanesulfonyloxy group.

In illustrative embodiments of the present invention there is provided a process described herein wherein $X^1$ is halogen.

In illustrative embodiments of the present invention there is provided a process described herein wherein $X^1$ is chloro or bromo.

In illustrative embodiments of the present invention there is provided a process described herein wherein $G^1$ is $—OR^1$.

In illustrative embodiments of the present invention there is provided a process described herein wherein $R^1$ is alkyl.

In illustrative embodiments of the present invention there is provided a process described herein wherein $R^1$ is methyl.

In illustrative embodiments of the present invention there is provided a process described herein wherein X and Y together form a single ring group with the two carbons to which they are bonded and are an oxygen atom; and $G^2$ is an azide, heterocyclic or substituted heterocyclic ring.

In illustrative embodiments of the present invention there is provided a process described herein wherein X and Y together form a single ring group with the two carbons to which they are bonded and $G^2$ is a heterocyclic or substituted heterocyclic ring.

In illustrative embodiments of the present invention there is provided a process described herein wherein X and Y together form a single ring group with the two carbons to which they are bonded and $G^2$ is phthalimide.

In illustrative embodiments of the present invention there is provided a process described herein wherein $G^2$ is an azide, heterocyclic or substituted heterocyclic ring.

In illustrative embodiments of the present invention there is provided a process described herein wherein $G^2$ is a heterocyclic or substituted heterocyclic ring.

In illustrative embodiments of the present invention there is provided a process described herein wherein $G^2$ is phthalimide.

In illustrative embodiments of the present invention there is provided a process described herein wherein $L^1$ is halogen and $G^1$ is $OR^1$.

In illustrative embodiments of the present invention there is provided a process described herein wherein $L^1$ is chloro and $R^1$ is alkyl.

In illustrative embodiments of the present invention there is provided a process described herein wherein $L^1$ is chloro and $R^1$ is methyl.

In illustrative embodiments of the present invention there is provided a process described herein wherein $L^1$ is halogen and $G^1$ is $OR^1$.

In illustrative embodiments of the present invention there is provided a process described herein wherein $L^1$ is chloro and $R^1$ is alkyl.

In illustrative embodiments of the present invention there is provided a process described herein wherein $L^1$ is chloro and $R^1$ is methyl.

In illustrative embodiments of the present invention there is provided a process described herein wherein X and Y together form a single ring group with the two carbons to which they are bonded and $G^2$ is an azide, heterocyclic or substituted heterocyclic ring.

In illustrative embodiments of the present invention there is provided a process described herein wherein X and Y together form a single ring group with the two carbons to which they are bonded and $G^2$ is a heterocyclic or substituted heterocyclic ring.

In illustrative embodiments of the present invention there is provided a process described herein wherein X and Y together form a single ring group with the two carbons to which they are bonded and $G^2$ is phthalimide.

In illustrative embodiments of the present invention there is provided a process described herein wherein $L^2$ is a sulfonyloxy group.

In illustrative embodiments of the present invention there is provided a process described herein wherein $L^2$ is a toluenesulfonyloxy, methanesulfonyloxy or trifluoromethanesulfonyloxy group.

In illustrative embodiments of the present invention there is provided a process described herein wherein $L^2$ is a halogen.

In illustrative embodiments of the present invention there is provided a process described herein wherein $L^2$ is chloro.

In illustrative embodiments of the present invention there is provided a process described herein wherein M is a metal and $G^2$ is an azide, heterocyclic or substituted heterocyclic ring.

In illustrative embodiments of the present invention there is provided a process described herein wherein M is sodium or potassium and $G^2$ is a heterocyclic or substituted heterocyclic ring.

In illustrative embodiments of the present invention there is provided a process described herein wherein M is potassium and $G^2$ is a phthalimide.

In illustrative embodiments of the present invention there is provided a process described herein wherein $L^2$ is a sulfonyloxy group.

In illustrative embodiments of the present invention there is provided a process described herein wherein $L^2$ is a toluenesulfonyloxy, methanesulfonyloxy or trifluoromethanesulfonyloxy group.

In illustrative embodiments of the present invention there is provided a process described herein wherein $L^2$ is a halogen.

In illustrative embodiments of the present invention there is provided a process described herein wherein $L^2$ is chloro.

In illustrative embodiments of the present invention there is provided a process described herein wherein (S)-Rivaroxaban is made.

In illustrative embodiments of the present invention there is provided a composition comprising Rivaroxaban and at least one of: N-methyl-phthalimide, ethanol, methylamine, and isopropanol.

In illustrative embodiments of the present invention there is provided a composition comprising Rivaroxaban and at least one of the compounds described herein.

Other aspects and features of the present invention will become apparent to those ordinarily skilled in the art upon review of the following description of specific embodiments of the invention in conjunction with the accompanying figures.

DETAILED DESCRIPTION

As used herein, the term "alkyl" by itself or as part of another substituent, means, unless otherwise stated, a saturated straight or branched chain, or cyclic hydrocarbon radical, or combination thereof having the number of carbon atoms designated (e.g. $C_1$-$C_{10}$ or 1- to 10-membered means one to ten carbons). When there is no indication of the number of carbon atoms in the alkyl, it is meant, unless otherwise indicated by context, that there are from 1 to 10 carbons. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like.

As used herein, the term "aryl" by itself or as part of another substituent, means, unless otherwise stated, a polyunsaturated, aromatic, hydrocarbon substituent which can be a single ring or multiple rings (often from 1 to 3 rings) which are fused together or linked covalently. "Aryl" includes, but is not limited to, "heteroaryl" groups. "Heteroaryl" refers to an aryl group that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include: phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridinyl, 3-pyridinyl, 4-pyridinyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. The term "aryl" when used in combination with other terms (e.g., aryloxy, arylthioxy, arylalkyl) includes both aryl and heteroaryl rings as defined herein. Thus, the term "arylalkyl" is meant to include those radicals in which an aryl group is attached to an alkyl group (e.g., benzyl, phenylethyl, pyridylmethyl, etc.) including those alkyl groups in which a carbon atom containing group (e.g., a methylene group) has been replaced by, for example, an oxygen atom (e.g., phenoxymethyl, 2-pyridyloxymethyl, 3-(1-naphthyloxy)propyl, etc).

As used herein, a "heterocyclic ring" means, unless otherwise stated, a 3 to 9 membered saturated or partially unsaturated, mono- or bicyclic, optionally benzo-fused ring having at least one heteroatom selected from S, N and O.

As used herein, a "protecting group" is a temporary group that is introduced into a molecule by chemical modification of a functional group in order to obtain chemoselectivity in a subsequent chemical reaction. For example, see T. W. Greene, P. G. M. Wuts, Protective Groups in Organic Synthesis; Wiley & Sons: New York, 1999. Non-limiting examples include arylalkyl, substituted arylalkyl, alkylsulfonyl, substituted alkylsulfonyl, arylsulfonyl, substituted arylsulfonyl, arylalkyl sulfonyl, substituted arylalkyl sulfonyl, alkylphosphonyl, substituted alkylphosphonyl, arylalkylphosphonyl, substituted arylalkylphosphonyl, arylphosphonyl, substituted arylphosphonyl, alkoxycarbonyl, substituted alkoxycarbonyl, aryloxycarbonyl, substituted aryloxycarbonyl, aralkyloxycarbonyl, substituted aralkyloxycarbonyl, alkylcarbonyl, substituted alkylcarbonyl, aralkylcarbonyl, substituted aralkylcarbonyl, arylcarbonyl and substituted arylcarbonyl.

As used herein, a "single ring group" is a single chemical moiety, that comprises at least one ring structure. The single chemical moiety will comprise a plurality of atoms and may comprise one or more rings that may be fused or otherwise covalently attached.

As used herein, a "primary amine precursor" means, unless otherwise stated, an amine bearing one or more temporary groups, which, when cleaved, regenerate the primary amine functionality. Non-limiting examples include —NR$^{2'}$R$^{3'}$, —N=C(R$^{4'}$)$_2$, and —N$_3$ wherein R$^{2'}$ and R$^{3'}$ are either two independent groups or together form a single ring group with the N to which they are bonded; R$^{2'}$ and R$^{3'}$, when independent groups, are independently selected from the group consisting of: hydrogen and a suitable amine protecting group, provided that both R$^{2'}$ and R$^{3'}$ are not both hydrogen; R$^{2'}$ and R$^{3'}$, when together, form a single ring group with the N to which they are bonded, are a heterocyclic ring, or a substituted heterocyclic ring such as phthalimide or saccharin; R$^{4'}$ is hydrogen, alkyl, substituted alkyl, aryl, substituted aryl, arylalkyl or substituted arylalkyl.

As used herein, a "primary amine formation agent" is an agent capable of releasing the temporary group from a primary amine precursor to release a primary amine function. For example, see T. W. Greene, P. G. M. Wuts, Protective Groups in Organic Synthesis; Wiley & Sons: New York, 1999. Non-limiting examples include hydrogen, hydride based reducing agents, metal catalyzed reducing agents, acids and R—NR$^4$R$^5$ wherein R is hydrogen, —OH, alkyl, substituted alkyl, aryl, substituted aryl, arylalkyl or substituted arylalkyl; R$^4$ and R$^5$ are either two independent groups or together form a single ring group with the N to which they are bonded; R$^4$ and R$^5$, when independent groups, are independently selected from the group consisting of: H, alkyl, substituted alkyl, aryl, substituted aryl, arylalkyl, substituted arylalkyl, amine and substituted amino; R$^4$ and R$^5$, when together form a single ring group with the N to which they are bonded, are a heteroaryl ring. In some embodiments, the primary amine formation agent is methylamine.

As used herein, the term "substituted" refers to the replacement of a hydrogen atom on a compound with a substituted group. A substituent may be a non-hydrogen atom or multiple atoms of which at least one is a non-hydrogen atom and one or more may or may not be hydrogen atoms. For example, without limitation, substituted compounds may comprise one or more substituent's selected from the group consisting of: R'', OR'', NR''R'', SR'', halogen, SiR''R'''R'''', OC(O)R'', C(O)R'', CO$_2$R'', CONR''R''', NR''''C(O)$_2$R'', S(O)R'', S(O)$_2$R'', CN, and NO$_2$. As used herein, each R'', R''', and R'''' may be selected, independently, from the group consisting of: hydrogen, halogen, oxygen, substituted or unsubstituted heteroalkyl, substituted or unsubstituted aryl, substituted or unsubstituted alkyl, alkoxy or thioalkoxy groups, and aralkyl groups.

In illustrative embodiments of the present invention, there is provided a compound of Formula 13:

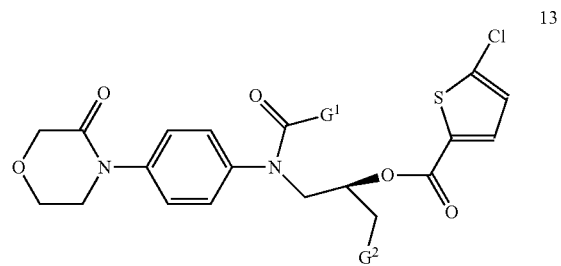

wherein
G$^1$ is OR$^1$, NR$^2$R$^3$ or CO$_3$;
R$^1$ is alkyl, substituted alkyl, aryl, substituted aryl, arylalkyl or substituted arylalkyl;
R$^2$ and R$^3$ are either (a) two independent groups or (b) together form a single ring group with the N to which they are bonded;
R$^2$ and R$^3$, when independent groups, are independently selected from the group consisting of: H, alkyl, substituted alkyl, aryl, substituted aryl, arylalkyl and substituted arylalkyl;
R$^2$ and R$^3$, when together form a single ring group with the N to which they are bonded, are a heteroaryl ring;
Q is halogen; and
G$^2$ is a primary amine precursor.

In some embodiments, the compound of Formula 13 is a compound in which G$^1$ is OR$^1$ and G$^2$ is an azide or NR$^{2'}$R$^{3'}$. In some embodiments, the compound of Formula 13 is a compound in which G$^1$ is OR$^1$ and G$^2$ is an azide, heterocyclic or substituted heterocyclic ring. In some embodiments, the compound of Formula 13 is a compound in which R$^1$ is alkyl and G$^2$ is a heterocyclic ring or a substituted heterocyclic ring. In some embodiments the compound of Formula 13 is a compound in which G$^1$ is methoxy and G$^2$ is phthalimide.

In illustrative embodiments of the present invention, there is provided a compound of Formula 13a:

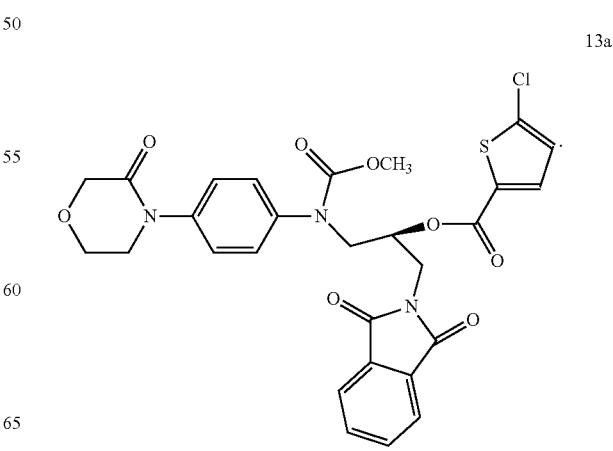

In illustrative embodiments of the present invention, there is provided a compound of Formula 14:

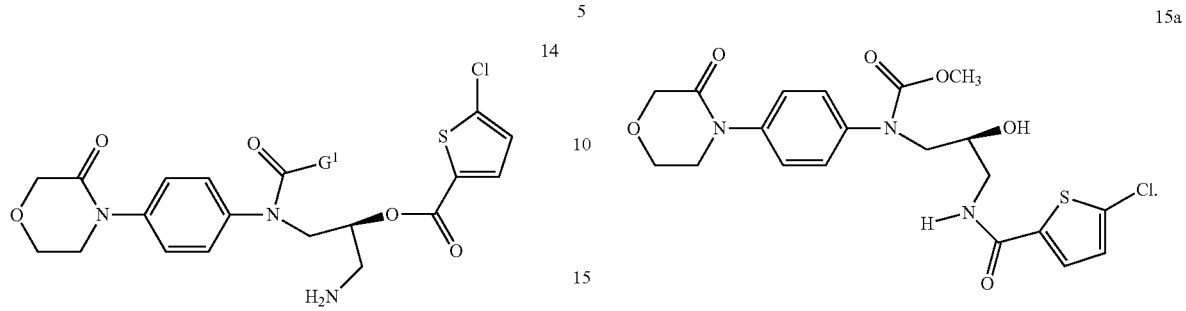

wherein G¹ may be any of the definitions for G¹ as set out above.

In illustrative embodiments of the present invention, there is provided a compound of Formula 14a:

In illustrative embodiments of the present invention, there is provided a compound of Formula 15:

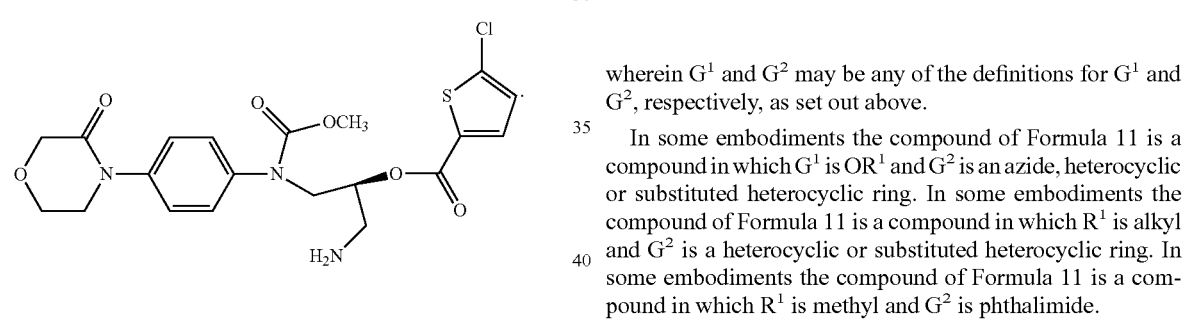

wherein G¹ may be any of the definitions for G¹ as set out above.

In illustrative embodiments of the present invention, there is provided a compound of Formula 15a:

In illustrative embodiments of the present invention, there is provided a compound of Formula 11:

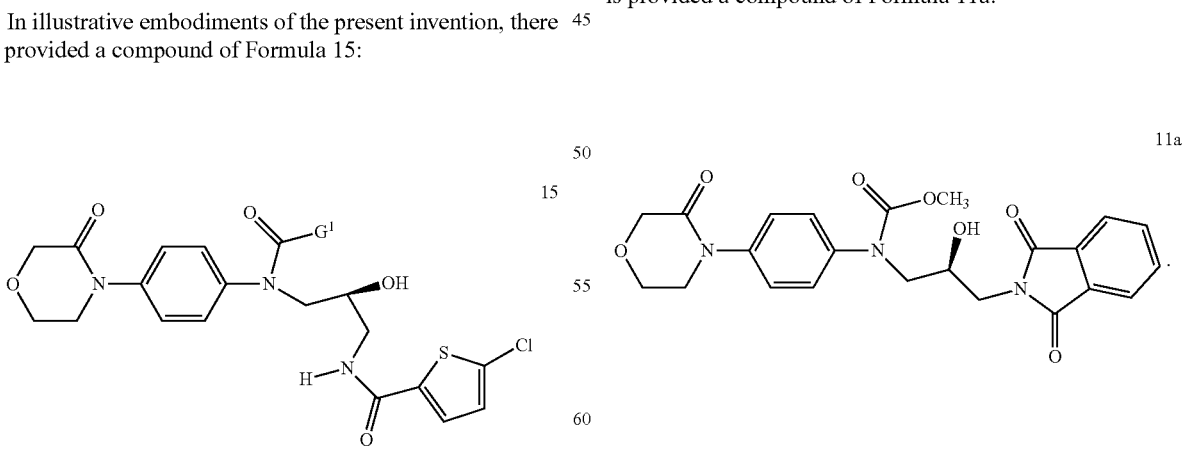

wherein G¹ and G² may be any of the definitions for G¹ and G², respectively, as set out above.

In some embodiments the compound of Formula 11 is a compound in which G¹ is OR¹ and G² is an azide, heterocyclic or substituted heterocyclic ring. In some embodiments the compound of Formula 11 is a compound in which R¹ is alkyl and G² is a heterocyclic or substituted heterocyclic ring. In some embodiments the compound of Formula 11 is a compound in which R¹ is methyl and G² is phthalimide.

In illustrative embodiments of the present invention, there is provided a compound of Formula 11a:

In illustrative embodiments of the present invention, R and/or S Rivaroxaban and intermediates thereof may be prepared by an exemplary process as set out in Scheme 1. Exemplary reagents and conditions for these reactions are disclosed herein.

Scheme 1

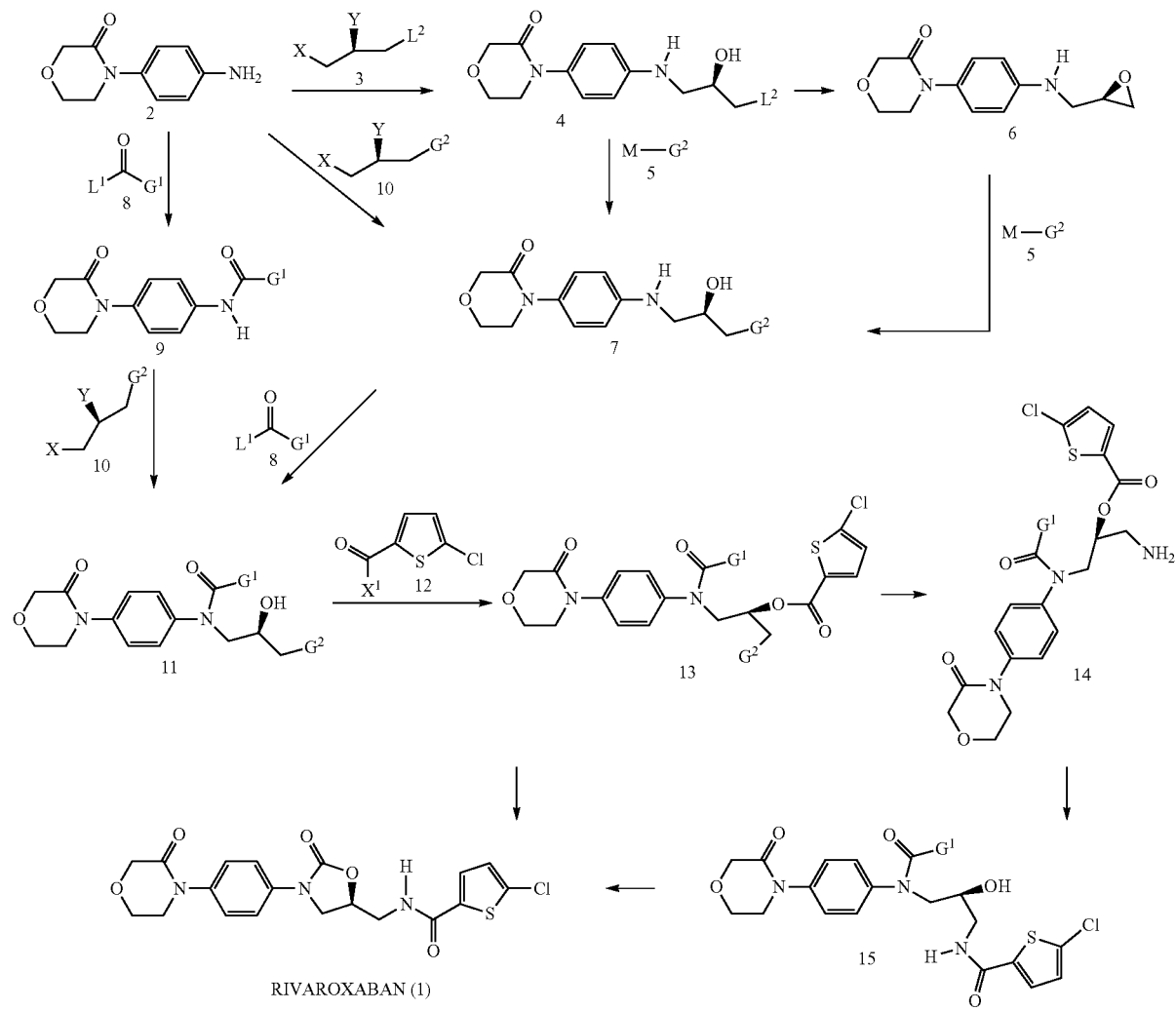

Appropriate choice of reagents will adapt the processes of the present invention to the preparation of the desired enantiomer of any of the compounds set out in Scheme 1. For example, the (R)-enantiomer of Rivaroxaban may be prepared by replacing an (R)-enantiomer of the compound of Formula 3 with an (S)-enantiomer of the same compound. Similarly, the stereochemistry of any of the stereospecific reactions may be controlled by selecting the appropriate reagents so that they have the desired stereochemistry.

According to illustrative embodiments of the present invention, there is provided a process for the preparation of (S)-Rivaroxaban comprising reacting, optionally in the presence of a first base, the compound of Formula 13 with a suitable primary amine formation agent.

The suitable primary amine formation agent may be determined by the primary amine precursor group. The suitable primary amine formation agent may be selected from the group consisting of hydrogen, hydride based reducing agents, metal catalyzed reducing agents, acids and R—NR$^4$R$^5$ wherein R is hydrogen, —OH, alkyl, substituted alkyl, aryl, substituted aryl, arylalkyl or substituted arylalkyl; R$^4$ and R$^5$ are either two independent groups or together form a single ring group with the N to which they are bonded; R$^4$ and R$^5$, when independent groups, are independently selected from the group consisting of: H, alkyl, substituted alkyl, aryl, substituted aryl, arylalkyl, substituted arylalkyl, amine and substituted amino; R$^4$ and R$^5$, when together form a single ring group with the N to which they are bonded, are a heteroaryl ring.

The first base may be inorganic or organic. The first base may be selected from the group consisting of metal hydroxides, carbonates, phosphates, tertiary amines, and aryl amines. The first base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline, N,N-diethylaniline, pyridine, n-butyl lithium, lithium diisopropylamide (LDA), lithium hexamethyldisilazide (LiHMDS), sodium hexamethyldisilazide (NaHMDS), potassium hexamethyldisilazide (KHMDS), sodium hydride (NaH), potassium hydride (KH), potassium tert-butoxide, and mixtures thereof.

The reaction of the compound of Formula 13 with the suitable primary amine formation agent may be conducted in a first solvent. The first solvent may be a suitable protic or aprotic organic solvent. The first solvent may be selected from the group consisting of alcohols (e.g. methanol, ethanol, propanol, isopropanol, butanol), alkyl ethers, aryl ethers, arylalkyl ethers (e.g. tetrahydrofuran, dioxane, diethyl ether, methyl t-butyl ether, diisopropyl ether, butyl ether, diphenyl ether, methylphenyl ether), alkyl esters (e.g. ethyl acetate, isopropyl acetate), alkyl ketones (e.g. acetone, methyl ethyl ketone, methyl isobutyl ketone), aromatic hydrocarbons, and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

When reacting the compound of Formula 13 with the suitable primary amine formation agent, the compound of Formula 14 and/or the compound of Formula 15 may be isolated. Particular variations of reaction conditions (e.g. temperature, primary amine formation agent, first base, solvent, etc) may permit isolation of the compounds of Formula 14 and/or 15. For example, use of mild reaction conditions (e.g. low temperature, mild base) may permit isolation of a compound of Formula 14. Application of heat to a compound of Formula 14, optionally in the presence of a first base, may permit isolation of a compound of Formula 15.

In illustrative embodiments of the present invention, there is provided a process for the preparation of the compound of Formula 13 comprising reacting, optionally in the presence of a second base, the compound of Formula 11 with a compound of Formula 12:

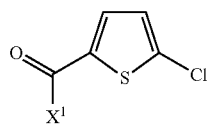

12 wherein $X^1$ is a leaving group selected from the group consisting of halogen, sulfonyloxy, imidazole, ester, $C_1$-$C_4$ alkoxy, substituted $C_1$-$C_4$ alkoxy, trihalomethoxy, N-hydroxysuccinimide, p-nitrophenol, N-hydroxyphthalimide, and N-hydroxybenzotriazole.

In some embodiments the compound of Formula 12 is a compound in which $X^1$ is sulfonyloxy group. In some embodiments the compound of Formula 12 is a compound in which $X^1$ is a toluenesulfonyloxy, methanesulfonyloxy or trifluoromethanesulfonyloxy group. In some embodiments the compound of Formula 12 is a compound in which $X^1$ is halogen. In some embodiments the compound of Formula 12 is a compound in which $X^1$ is chloro or bromo.

The second base may be inorganic or organic. The second base may be selected from the group consisting of metal hydroxides, carbonates, phosphates, tertiary amines, and aryl amines. The second base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, diisopropylethylamine. N,N-dimethylaniline, N,N-diethylaniline, pyridine, 4-(dimethylamino)pyridine, 1,8-diazabicyclo[5.4.0]undec-7-ene (DBU), 1,5-diazabicyclo[4.3.0]non-5-ene (DBN), n-butyl lithium, lithium diisopropylamide (LDA), lithium hexamethyldisilazide (LiHMDS), sodium hexamethyldisilazide (NaHMDS), potassium hexamethyldisilazide (KHMDS), sodium hydride (NaH), potassium hydride (KH), potassium tert-butoxide, and mixtures thereof.

The reaction of the compound of Formula 11 with the compound of Formula 12 may be conducted in a second solvent. The second solvent may be selected from the group consisting of alkyl ethers, aryl ethers, arylalkyl ethers (e.g. tetrahydrofuran, dioxane, diethyl ether, methyl t-butyl ether, diisopropyl ether, butyl ether, diphenyl ether, methylphenyl ether), alkyl esters (e.g. ethyl acetate, isopropyl acetate), alkyl ketones (e.g. acetone, methyl ethyl ketone, methyl isobutyl ketone), aromatic hydrocarbons, and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

There are two general methods by which the compound of Formula 11 may be prepared. One alternative is to prepare the compound of Formula 11 from a compound of Formula 9:

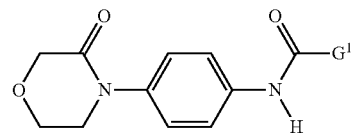

9 wherein $G^1$ may be any of the definitions for $G^1$ as set out above.

In some embodiments the compound of Formula 9 is a compound in which $G^1$ is —$OR^1$. In some embodiments the compound of Formula 9 is a compound in which $R^1$ is alkyl. In some embodiments the compound of Formula 9 is a compound in which $R^1$ is methyl.

Forming the compound of Formula 11 may be achieved by reacting, optionally in the presence of a third base, the compound of Formula 9 with a compound of Formula 10:

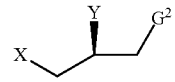

10 wherein

X and Y are either i) separate groups or ii) together form a single ring group with the two carbons to which they are bonded; and when:

i) X and Y are separate groups, X is a halogen and Y is —OH; or ii) X and Y together form a single ring group with the two carbons to which they are bonded, they are an oxygen atom; and $G^2$ may be any of the definitions for $G^2$ as set out above.

In some embodiments the compound of Formula 10 is a compound in which X is a halogen, Y is —OH and $G^2$ is an azide, heterocyclic or substituted heterocyclic ring. In some embodiments the compound of Formula 10 is a compound in which X is Cl, Y is —OH and $G^2$ is a heterocyclic or substituted heterocyclic ring. In some embodiments the compound of Formula 10 is a compound in which X is Cl, Y is —OH and $G^2$ is phthalimide. In some embodiments the compound of Formula 10 is a compound in which X and Y together form a single ring group and are an oxygen atom and $G^2$ is an azide, heterocyclic or substituted heterocyclic ring. In some embodiments the compound of Formula 10 is a compound in which X and Y together form a single ring group and are an oxygen atom and $G^2$ is a heterocyclic or substituted heterocyclic ring. In some embodiments the compound of Formula 10 is a compound in which X and Y together form a single ring group and are an oxygen atom and $G^2$ is phthalimide.

The third base may be inorganic or organic. The third base may be selected from the group consisting of metal hydroxides, carbonates, phosphates, tertiary amines, and aryl amines. The third base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline, N,N-diethylaniline, pyridine, n-butyl lithium, lithium diisopropylamide (LDA), lithium hexamethyldisilazide (LiHMDS), sodium hexamethyldisilazide (NaHMDS), potassium hexamethyldisilazide (KHMDS), sodium hydride (NaH), potassium hydride (KH), potassium tert-butoxide, and mixtures thereof.

The reaction of the compound of Formula 9 with the compound of Formula 10 may be conducted in a third solvent. The third solvent may be selected from the group consisting of alcohols (e.g. methanol, ethanol, n-propanol, isopropanol, butanol), alkyl ethers, aryl ethers, arylalkyl ethers (e.g. tetrahydrofuran, dioxane, diethyl ether, methyl t-butyl ether, diisopropyl ether, butyl ether, diphenyl ether, methylphenyl ether), alkyl esters (e.g. ethyl acetate, isopropyl acetate), alkyl ketones (e.g. acetone, methyl ethyl ketone, methyl isobutyl ketone), aromatic hydrocarbons, and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

Alternatively, the compound of Formula 11 may be prepared from a compound of Formula 7:

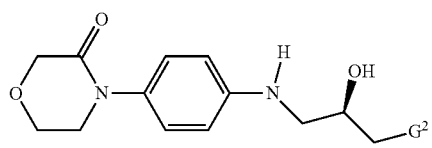

7 wherein $G^2$ may be any of the definitions for $G^2$ as set out above.

In some embodiments the compound of Formula 7 is a compound in which $G^2$ is an azide, heterocyclic or substituted heterocyclic ring. In some embodiments the compound of Formula 7 is a compound in which $G^2$ is a heterocyclic or substituted heterocyclic ring. In some embodiments the compound of Formula 7 is a compound in which $G^2$ is phthalimide.

Forming the compound of Formula 11 may be achieved by reacting, optionally in the presence of a fourth base, the compound of Formula 7 with a compound of Formula 8:

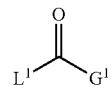

8 wherein
$L^1$ is a leaving group selected from the group consisting of halogen, imidazole, ester. $C_1$-$C_4$ alkoxy, trihalomethoxy, N-hydroxysuccinimide, p-nitrophenol, N-hydroxyphthalimide, and N-hydroxybenzotriazole; and $G^1$ may be any of the definitions for $G^1$ as set out above.

In some embodiments the compound of Formula 8 is a compound in which $L^1$ is halogen and $G^1$ is $OR^1$. In some embodiments the compound of Formula 8 is a compound in which $L^1$ is chloro and $R^1$ is alkyl. In some embodiments the compound of Formula 8 is a compound in which $L^1$ is chloro and $R^1$ is methyl.

The fourth base may be inorganic or organic. The fourth base may be selected from the group consisting of metal hydroxides, carbonates, phosphates, tertiary amines, and aryl amines. The fourth base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, diisopropylethylamine, N,N-dimethylaniline, N,N-diethylaniline, pyridine, and mixtures thereof.

The reaction of the compound of Formula 7 with the compound of Formula 8 may be conducted in a fourth solvent. The fourth solvent may be selected from the group consisting of water, alcohols (e.g. methanol, ethanol, n-propanol, isopropanol, butanol), alkyl ethers, aryl ethers, arylalkyl ethers (e.g. tetrahydrofuran, dioxane, diethyl ether, methyl t-butyl ether, diisopropyl ether, butyl ether, diphenyl ether, methylphenyl ether), alkyl esters (e.g. ethyl acetate, isopropyl acetate), alkyl ketones (e.g. acetone, methyl ethyl ketone, methyl isobutyl ketone), aromatic hydrocarbons, and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

The compounds of Formula 9 and 7 may be prepared, using different methods, from a compound of Formula 2:

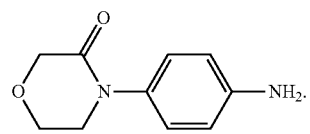

2

The compound of Formula 9 may be prepared from the compound of Formula 2 by reacting the compound of Formula 2 with the compound of Formula 8. Similar conditions may be used in the reaction between the compounds of Formula 2 and 8 as are used in the reaction between the compounds of Formula 7 and 8.

The compound of Formula 7 may be prepared from the compound of Formula 2 by reacting the compound of Formula 2 with the compound of Formula 10. Similar conditions may be used in the reaction between the compounds of Formula 2 and 10 as are used in the reaction between the compounds of Formula 9 and 10, except that weaker base conditions may be applied.

Alternatively, the compound of Formula 7 may be prepared from a compound of Formula 4 and/or a compound of Formula 6:

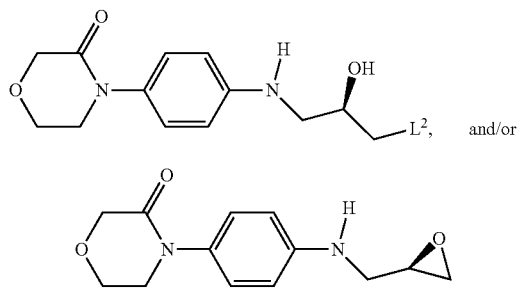

wherein $L^2$ is a halogen or sulfonyloxy group.

In some embodiments the compound of Formula 4 is a compound in which $L^2$ is a sulfonyloxy group. In some embodiments the compound of Formula 4 is a compound in which $L^2$ is a toluenesulfonyloxy, methanesulfonyloxy or trifluoromethanesulfonyloxy group. In some embodiments the compound of Formula 4 is a compound in which $L^2$ is a halogen. In some embodiments the compound of Formula 4 is a compound in which $L^2$ is chloro.

The compound of Formula 7 may be prepared by reacting, optionally in the presence of a fifth base, the compound of Formula 4 or the compound of Formula 6 with a compound of Formula 5:

wherein

M is H or a metal selected from the group consisting of Li, Na and K; and $G^2$ may be any of the definitions for $G^2$ as set out above.

In some embodiments the compound of Formula 5 is a compound in which M is a metal and $G^2$ is an azide, heterocyclic or substituted heterocyclic ring. In some embodiments the compound of Formula 5 is a compound in which M is sodium or potassium and $G^2$ is a heterocyclic or substituted heterocyclic ring. In some embodiments the compound of Formula 5 is a compound in which M is potassium and $G^2$ is a phthalimide.

The fifth base may be inorganic or organic. The fifth base may be selected from the group consisting of metal hydroxides, carbonates, phosphates, tertiary amines, and aryl amines. The fifth base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline, N,N-diethylaniline, pyridine, n-butyl lithium, lithium diisopropylamide (LDA), lithium hexamethyldisilazide (LiHMDS), sodium hexamethyldisilazide (NaHMDS), potassium hexamethyldisilazide (KHMDS), sodium hydride (NaH), potassium hydride (KH), potassium tert-butoxide, and mixtures thereof.

The reaction of the compound of Formula 4 or 6 with the compound of Formula 5 may be conducted in a fifth solvent. The fifth solvent may be selected from the group consisting of water, alcohols (e.g. methanol, ethanol, n-propanol, isopropanol, butanol), alkyl ethers, aryl ethers, arylalkyl ethers (e.g. tetrahydrofuran, dioxane, diethyl ether, methyl t-butyl ether, diisopropyl ether, butyl ether, diphenyl ether, methylphenyl ether), alkyl esters (e.g. ethyl acetate, isopropyl acetate), alkyl ketones (e.g. acetone, methyl ethyl ketone, methyl isobutyl ketone), aromatic hydrocarbons, and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

In some embodiments, the compound of Formula 6 may be prepared from the compound of Formula 4 by reacting the compound of Formula 4 with a sixth base. The sixth base may be inorganic or organic. The sixth base may be selected from the group consisting of metal hydroxides, carbonates, phosphates, tertiary amines, and aryl amines. The sixth base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline, N,N-diethylaniline, pyridine, and mixtures thereof.

The reaction of compound of Formula 4 with the sixth base to give the compound of Formula 6 may be conducted in a sixth solvent. The sixth solvent may be selected from the group consisting of water, alcohols (e.g. methanol, ethanol, n-propanol, isopropanol, butanol), alkyl ethers, aryl ethers, arylalkyl ethers (e.g. tetrahydrofuran, dioxane, diethyl ether, methyl t-butyl ether, diisopropyl ether, butyl ether, diphenyl ether, methylphenyl ether), alkyl esters (e.g. ethyl acetate, isopropyl acetate), alkyl ketones (e.g. acetone, methyl ethyl ketone, methyl isobutyl ketone), aromatic hydrocarbons, and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

The compound of Formula 4 may be prepared from the compound of Formula 2 by reacting, optionally in the presence of a seventh base, the compound of Formula 2 with a compound of Formula 3:

wherein X, Y and $L^2$ may be any of the definitions for X, Y and $L^2$, respectively, as set out above.

In some embodiments the compound of Formula 3 is a compound in which $L^2$ is a sulfonyloxy group. In some embodiments the compound of Formula 3 is a compound in which $L^2$ is a toluenesulfonyloxy, methanesulfonyloxy or trifluoromethanesulfonyloxy group. In some embodiments the compound of Formula 3 is a compound in which $L^2$ is a halogen. In some embodiments the compound of Formula 3 is a compound in which L² is chloro.

The seventh base may be inorganic or organic. The seventh base may be selected from the group consisting of metal hydroxides, carbonates, phosphates, tertiary amines, and aryl amines. The seventh base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-dimethylaniline, N,N-diethylaniline, pyridine, and mixtures thereof.

The reaction of the compound of Formula 2 with the compound of Formula 3 may be conducted in a seventh solvent. The seventh solvent may be selected from the group consisting of water, alcohols (e.g. methanol, ethanol, n-propanol, isopropanol, butanol), alkyl ethers, aryl ethers, arylalkyl ethers (e.g. tetrahydrofuran, dioxane, diethyl ether, methyl t-butyl ether, diisopropyl ether, butyl ether, diphenyl ether, methylphenyl ether), alkyl esters (e.g. ethyl acetate, isopropyl acetate), alkyl ketones (e.g. acetone, methyl ethyl ketone, methyl isobutyl ketone), aromatic hydrocarbons, and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof.

In illustrative embodiments of the present invention, Rivaroxaban and the intermediates thereof may be prepared by an exemplary process as set out in Scheme 2. Exemplary reagents and conditions for these reactions are disclosed herein.

Scheme 2

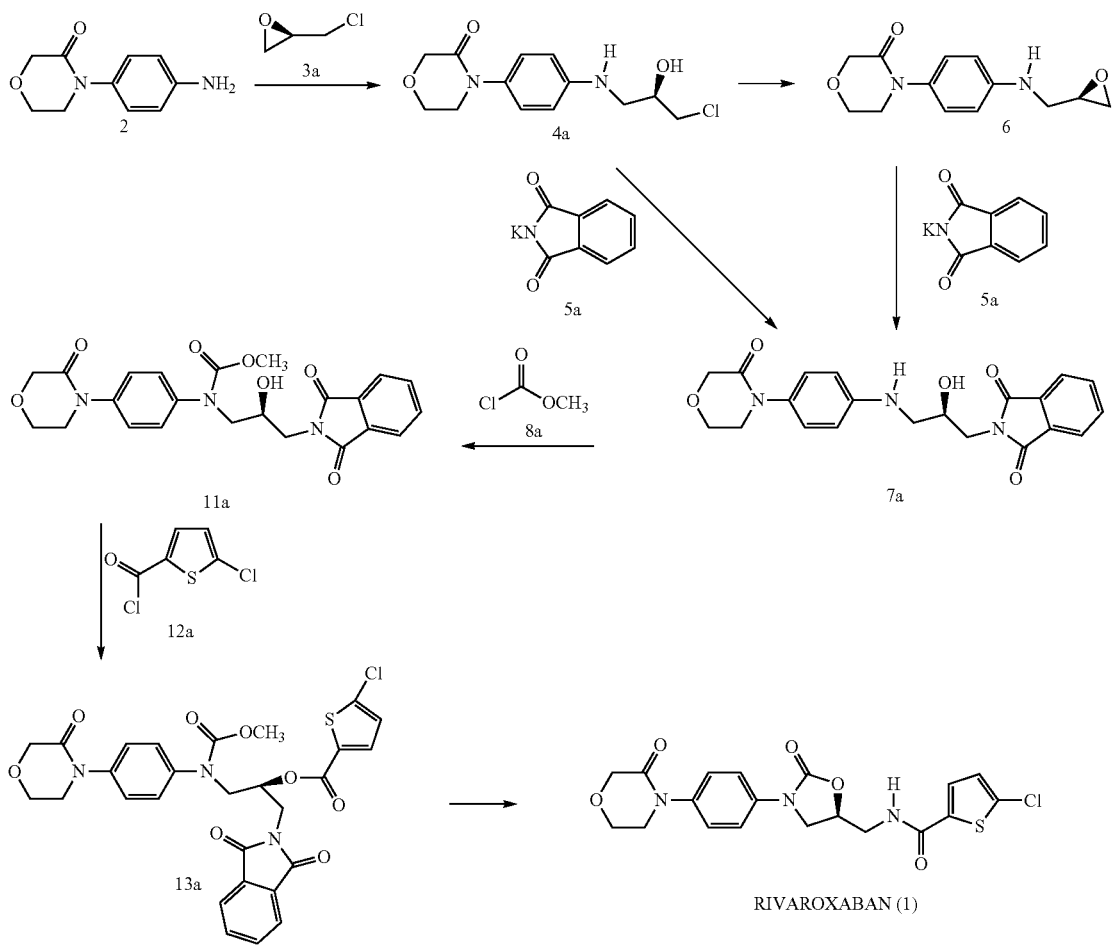

RIVAROXABAN (1)

EXAMPLES

The following examples are illustrative of some of the embodiments of the invention described herein. These examples should not be considered to limit the spirit or scope of the invention in any way.

Example 1

Preparation of 4-[4-(N-(3-chloro-2R-hydroxy-1-propyl) amino)phenyl]morpholin-3-one(4a): (R)-(−)-Epichlorohydrin (39.1 mL, 499.45 mmoL) was added in 6 portions over a period of 8 h to a refluxing suspension of 4-(4-aminophenyl)-3-morpholinone (60 g, 312.158 mmoL) in IPA (420 mL) under stirring. The reaction mixture was cooled to room temperature over a period of 4 h, and stirred further at room temperature for 2 h. The thick white suspension was filtered through a Buchner funnel. The solid was washed with IPA (2×60 mL) and dried under vacuum at 50° C. for 12 h to obtain 4-[4-(N-(3-chloro-2R-hydroxy-1-propyl)amino)phenyl] morpholin-3-one (62.22 g, 70%) as a crystalline white solid.

$^1$HNMR (300 MHz, CDCl$_3$) δ 2.80 (d, J=5.1 Hz, 1H), 3.15-3.22 (m, 1H), 3.33-3.38 (m, 1H), 3.57-3.71 (m, 4H), 3.96-4.05 (m, 3H), 4.17 (br s, 1H), 4.32 (s, 2H), 6.60-6.65 (m, 2H), 7.07-7.11 (m, 2H).

Example 2

Preparation of 4-[4-(N-(2R,3-epoxy-1-propyl)amino)phenyl]morpholin-3-one(6): NaOH (4.45 g, 50 wt % in water, 55.63 mmoL) in water (15 mL) was added to a suspension of 4-[4-(N-(3-chloro-2R-hydroxy-1-propyl)amino)phenyl] morpholin-3-one (14.4 g, 50.572 mmoL) in CH$_2$Cl$_2$ (100 mL) at room temperature. The biphasic mixture was stirred at room temperature for 6 h and the organic layer was separated, washed with water (1×30 mL) followed by brine (1×15 mL). The organic extract was dried (Na$_2$SO$_4$), filtered and concentrated to 45 mL. The solution was heated to reflux and heptane (90 mL) was charged over ca. 30 min. The mixture was cooled to room temperature over a period of 4 h and stirred at that temperature for another 2 h. The solids were filtered through a Buchner funnel and washed with CH$_2$Cl$_2$-heptane (1:3, 30 mL). The solids were dried at room temperature under vacuum for 12 h to obtain 4-[4-(N-(2R,3-epoxy-1-propyl)amino)phenyl]morpholin-3-one (12.05 g, 96%) as a crystalline off-white solid.

$^1$HNMR (300 MHz, CDCl$_3$) δ 2.69 (dd. J=5.0, 2.2 Hz, 1H), 2.82 (t, J=4.3 Hz, 1H), 3.20-3.27 (m, 2H), 3.51-3.58 (m, 1H), 3.67-3.71 (m, 2H), 3.98-4.02 (m, 3H), 4.32 (s, 2H), 6.66 (d, J=8.7 Hz, 2H), 7.11 (d, J=8.7 Hz, 2H).

Example 3

Preparation of 2-((2R)-2-Hydroxy-3-{[4-(3-oxomorpholin-4-yl)-phenyl]amino}propyl)-1H-isoindole-1,3(2H)-dione (7a): Potassium phthalimide (7.16 g, 38.632 mmoL) was added in one portion to a mechanically stirred mixture of 4-[4-(N-(3-chloro-2R-hydroxy-1-propyl)amino)phenyl] morpholin-3-one (10 g, 35.119 mmoL) in DMF (60 mL). The suspension was stirred at room temperature and was heated to 100° C., stirred at that temperature for 3 h and then cooled to room temperature. Water (60 mL) was charged and the suspension stirred for another 15 min. The suspension was filtered through a Buchner funnel. The solid was washed with water (2×40 mL) and dried under vacuum at 50° C. for 10 h to yield 2-((2R)-2-Hydroxy-3-{[4-(3-oxomorpholin-4-yl)-phenyl]amino}propyl)-1H-isoindole-1,3(2H)-dione (12.55 g, 93%) as a crystalline white solid.

$^1$HNMR (400 MHz, DMSO-d6) δ2.99-3.05 (m, 1H), 3.14-3.2 (m, 1H), 3.59-3.69 (m, 4H), 3.91-3.94 (m, 2H), 3.97-4.05 (m, 1H), 4.14 (s, 2H), 5.16 (d, J=5.2 Hz, 1H), 5.66 (t, J=6.0 Hz, 1H), 6.61 (d, J=8.7 Hz, 2H), 7.03 (d, J=8.8 Hz, 2H), 7.82-7.88 (m, 4H).

Example 4

Preparation of methyl (S)-2-hydroxy-3-(1,3-dioxoisoindolin-2-yl)propyl-4-(3-oxomorpholino)phenylcarbamate (11a): N,N-Diisopropylethylamine (14.32 mL, 82.193 mmoL) was added over 3 min to a stirred suspension of 2-((2R)-2-Hydroxy-3-{[4-(3-oxomorpholin-4-yl)-phenyl] amino}propyl)-1H-isoindole-1,3(2H)-dione (25 g, 63.225 mmoL) in acetonitrile (450 mL). Methyl chloroformate (8a) (5.9 mL, 75.87 mmoL) was added over a period of 3 min and the reaction mixture was stirred at room temperature for 4 h during which time the reaction mixture becomes homogeneous. The solvent was evaporated on a rotary evaporator and CH$_2$Cl$_2$ (150 mL) was charged. The solution was washed with 2% aqueous HCl (1×50 mL) followed by water (1×50 mL) and brine (1×25 mL). The organic layer was dried (Na$_2$SO$_4$) and evaporated. The residue was purified by flash chromatography over silica gel (4×12 cm) using EtOAc to obtain methyl (S)-2-hydroxy-3-(1,3-dioxoisoindolin-2-yl)propyl-4-(3-oxomorpholino)phenylcarbamate (27.8 g, 97%) as a crystalline solid.

$^1$HNMR (400 MHz, CDCl$_3$) δ 3.27 (br s, 1H, —OH), 3.67 (s, 3H), 3.76-3.86 (m, 6H), 4.02-4.04 (m, 2H), 4.07-4.14 (m, 1H), 4.33 (s, 2H), 7.31-7.36 (m, 4H), 7.71-7.75 (m, 2H), 7.83-7.87 (m, 2H).

Example 5

Preparation of 5-Chloro-thiophene-2-carboxylic acid-1-(1,3-dioxo-1,3-dihydro-isoindol-2-ylmethyl)-2-{methoxycarbonyl-[4-(3-oxo-morpholin-4-yl)-phenyl]-amino}-ethyl ester (13a): Oxalyl chloride (8.35 mL, 95.709 mmoL) was added over 3 min to a stirred and cooled (0° C.) suspension of 5-chlorothiophene-2-carboxylic acid (11.46 g, 68.364 mmoL) in CH$_2$Cl$_2$ (172 mL). DMF (0.1 mL) was added and the cooling bath was removed after 1 h. The reaction mixture becomes homogeneous over a period of 2 h after which the solvent was evaporated on a rotary evaporator and the residue was dried for 0.5 h on an oil pump vacuum to yield 12a. The residue was then dissolved in CH$_2$Cl$_2$ (50 mL) and added over 5 min to a stirred and cooled (0° C.) mixture of methyl (S)-2-hydroxy-3-(1,3-dioxoisoindolin-2-yl)propyl-4'(3' oxomorpholino)phenylcarbamate (24.8 g, 54.69 mmoL), N,N-diisopropylethylamine (14.3 mL, 82.04 mmoL) and 4-dimethylamino pyridine (335 mg, 2.74 mmoL) in CH$_2$Cl$_2$ (175 mL). The cooling bath was not recharged and stirring was continued overnight. The reaction mixture was washed with 2% aqueous HCl (50 mL), water (50 mL) and brine (25 mL). The organic layer was dried (Na$_2$SO$_4$) and evaporated. The residue was purified by flash chromatography over silica gel (4×12 cm) using EtOAc to obtain 5-Chloro-thiophene-2-carboxylic acid-1-(1,3-dioxo-1,3-dihydro-isoindol-2-ylmethyl)-2-{methoxycarbonyl-[4-(3-oxo-morpholin-4-yl)-phenyl}-amino]-ethyl ester (13a) (32.4 g, 99%) as a crystalline solid.

$^1$HNMR (300 MHz, CDCl$_3$) δ 3.68-3.70 (m, 5H), 3.94-4.04 (m, 5H), 4.11-4.16 (m, 1H), 4.32 (s, 2H), 5.50 (br m, 1H), 6.86 (d, J=3.9 Hz, 1H), 7.24-7.30 (m, 4H), 7.37 (d, J=3.9 Hz, 1H), 7.70-7.73 (m, 2H), 7.81-7.84 (m, 2H).

Example 6

Preparation of (S)-Rivaroxaban: Methylamine (390 mg, 40% in water) in EtOH (0.4 mL) was added to a stirred mixture of 5-Chloro-thiophene-2-carboxylic acid-1-(1,3-dioxo-1,3-dihydro-isoindol-2-ylmethyl)-2-{methoxycarbonyl-[4-(3-oxo-morpholin-4-yl)-phenyl]amino}-ethyl ester (13a) (1.2 g, 2 mmoL) in EtOH (4.8 mL). The mixture was heated to 60° C. for 4 h and cooled to room temperature. The precipitated solids were filtered, washed with EtOH (2×1.2 mL) and dried at 50° C. for 10 h to obtain Rivaroxaban (495 mg, 57%) as a crystalline white solid.

$^1$HNMR (300 MHz, DMSO-d6) δ3.59-3.62 (m, 2H), 3.69-3.73 (m, 2H), 3.85 (dd, J=8.9, 6.3 Hz, 1H), 3.95-3.99 (m, 2H), 4.16-4.22 (m, 1H), 4.19 (s, 2H), 4.82-4.86 (m, 1H), 7.19 (d, J=4.2 Hz, 1H), 7.40 (d, J=8.7 Hz, 2H), 7.56 (d, J=8.7 Hz, 2H), 7.69 (d, J=4.2 Hz, 1H), 8.97 (t, J=5.5 Hz, 1H).

Example 7

Methylamine (315 mg, 40% in water) in THF (0.8 mL) was added to a stirred mixture of 5-Chloro-thiophene-2-carboxylic acid-1-(1,3-dioxo-1,3-dihydro-isoindol-2-ylmethyl)-2-{methoxycarbonyl-[4-(3-oxo-morpholin-4-yl)-phenyl]-amino}-ethyl ester (13a) (800 mg, 1.337 mmol) in THF (4 mL). The mixture was heated to 60° C. for 20 h and cooled to room temperature. The precipitated solids were filtered, washed with THF (2×1.6 mL) and dried at 50° C. for 10 h to obtain Rivaroxaban (335 mg, 58%) as a crystalline white solid.

$^1$HNMR (300 MHz, DMSO-d6) δ3.59-3.62 (m, 2H), 3.69-3.73 (m, 2H), 3.85 (dd, J=8.9, 6.3 Hz, 1H), 3.95-3.99 (m, 2H), 4.16-4.22 (m, 1H), 4.19 (s, 2H), 4.82-4.86 (m, 1H), 7.19 (d, J=4.2 Hz, 1H), 7.40 (d, J=8.7 Hz, 2H), 7.56 (d, J=8.7 Hz, 2H), 7.69 (d, J=4.2 Hz, 1H), 8.97 (t, J=5.5 Hz, 1H).

Example 8

Methylamine (390 mg, 40% in water) in IPA (1 mL) was added to a stirred mixture of 5-Chloro-thiophene-2-carboxylic acid-1-(1,3-dioxo-1,3-dihydro-isoindol-2-ylmethyl)-2-{methoxycarbonyl-[4-(3-oxo-morpholin-4-yl)-phenyl]-amino}-ethyl ester (13a) (1 g, 1.672 mmol) and anhydrous $K_2CO_3$ (12 mg, 0.084 mmol) in IPA (6 mL). The mixture was heated to 60° C. for 15 h and cooled to room temperature. The precipitated solids were filtered, washed with IPA (2×1mL) followed by water (2×2 mL), IPA (1 mL) and dried at 50° C. for 10 h to obtain Rivaroxaban (628 mg, 86%) as a crystalline white solid.

$^1$HNMR (300 MHz, DMSO-d6) δ3.59-3.62 (m, 2H), 3.69-3.73 (m, 2H), 3.85 (dd, J=8.9, 6.3 Hz, 1H), 3.95-3.99 (m, 2H), 4.16-4.22 (m, 1H), 4.19 (s, 2H), 4.82-4.86 (m, 1H), 7.19 (d, J=4.2 Hz, 1H), 7.40 (d, J=8.7 Hz, 2H), 7.56 (d, J=8.7 Hz, 2H), 7.69 (d, J=4.2 Hz, 1H), 8.97 (t, J=5.5 Hz, 1H).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A process for the preparation of (S)- or (R)-Rivaroxaban comprising reacting a primary amine formation agent with a compound of Formula 13':

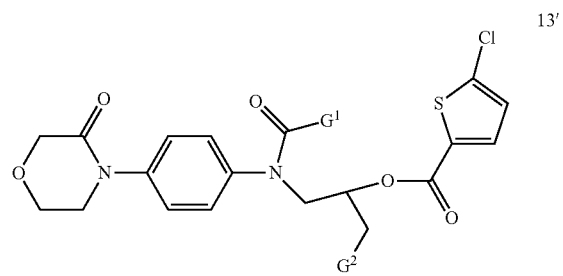

13' wherein
$G^1$ is $OR^1$, $NR_2R_3$ or $CQ_3$;
$R^1$ is alkyl, substituted alkyl, aryl, substituted aryl, arylalkyl or substituted arylalkyl;
$R^2$ and $R^3$ are either (a) two independent groups or (b) together form a single ring group with the N to which they are bonded;
$R^2$ and $R^3$, when independent groups, are independently selected from the group consisting of: H, alkyl, substituted alkyl, aryl, substituted aryl, arylalkyl and substituted arylalkyl;
$R^2$ and $R^3$, when together form a single ring group with the N to which they are bonded, are a heteroaryl ring;
Q is halogen; and
$G^2$ is a primary amine precursor.

2. The process of claim 1 wherein the suitable primary amine formation agent is selected from the group consisting of: hydrogen, hydride based reducing agents, metal catalyzed reducing agents, acids and R—$NR^4R^5$ wherein R is hydrogen, —OH, alkyl, substituted alkyl, aryl, substituted aryl, arylalkyl or substituted arylalkyl; $R^4$ and $R^5$ are either two independent groups or together form a single ring group with the N to which they are bonded; $R^4$ and $R^5$, when independent groups, are independently selected from the group consisting of: H, alkyl, substituted alkyl, aryl, substituted aryl, arylalkyl, substituted arylalkyl, amine and substituted amino; and $R^4$ and $R^5$, when together form a single ring group with the N to which they are bonded, are a heteroaryl ring.

3. The process of claim 1 further comprising reacting a compound of Formula 11':

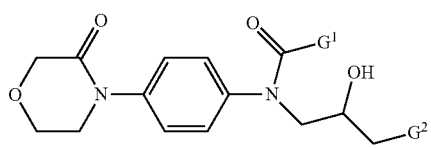

11' with a compound of Formula 12:

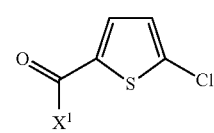

12 thereby forming the compound of Formula 13' wherein
G¹ is OR¹, NR²R³ or CQ₃;
R¹ is alkyl, substituted alkyl, aryl, substituted aryl, arylalkyl or substituted arylalkyl;
R² and R³ are either (a) two independent groups or (b) together form a single ring group with the N to which they are bonded;
R² and R³, when independent groups, are independently selected from the group consisting of: H, alkyl, substituted alkyl, aryl, substituted aryl, arylalkyl and substituted arylalkyl;
R² and R³, when together form a single ring group with the N to which they are bonded, are a heteroaryl ring;
Q is halogen;
G² is a primary amine precursor; and
X¹ is a leaving group selected from the group consisting of halogen, sulfonyloxy, imidazole, ester, C₁-C₄ alkoxy, substituted C₁-C₄ alkoxy, trihalomethoxy, N-hydroxysuccinimide, p-nitrophenol, N-hydroxyphthalimide, and N-hydroxybenzotriazole.

4. The process of claim 3 further comprising reacting a compound of Formula 9:

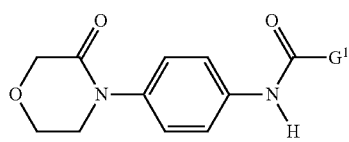

9 with a compound of Formula 10':

10' thereby forming the compound of Formula 11'
wherein
G² is OR¹, NR²R³ or CQ₃;
R¹ is alkyl, substituted alkyl, aryl, substituted aryl, arylalkyl or substituted arylalkyl;
R² and R³ are either (a) two independent groups or (b) together form a single ring group with the N to which they are bonded;
R² and R³, when independent groups, are independently selected from the group consisting of: H, alkyl, substituted alkyl, aryl, substituted aryl, arylalkyl and substituted arylalkyl;
R² and R³, when together form a single ring group with the N to which they are bonded, are a heteroaryl ring;
Q is halogen;
X and Y are either i) separate groups or ii) together form a single ring group with the two carbons to which they are bonded; and when: i) X and Y are separate groups, X is a halogen and Y is —OH; or ii) X and Y together form a single ring group with the two carbons to which they are bonded, they are an oxygen atom; and
G² is a primary amine precursor.

5. The process of claim 3 further comprising reacting a compound of Formula 7':

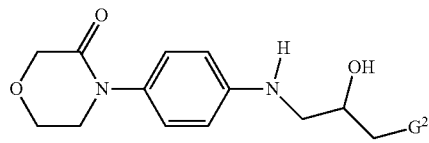

7' with a compound of Formula 8:

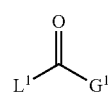

8 thereby forming the compound of Formula 11'
wherein
L¹ is a leaving group selected from the group consisting of: halogen, imidazole, ester, C₁-C₄ alkoxy, trihalomethoxy, N-hydroxysuccinimide, p-nitrophenol, N-hydroxyphthalimide, and N-hydroxybenzotriazole;
G¹ is OR¹, NR²R³ or CQ₃;
R¹ is alkyl, substituted alkyl, aryl, substituted aryl, arylalkyl or substituted arylalkyl;
R² and R³ are either (a) two independent groups or (b) together form a single ring group with the N to which they are bonded;
R² and R³, when independent groups, are independently selected from the group consisting of: H, alkyl, substituted alkyl, aryl, substituted aryl, arylalkyl and substituted arylalkyl;
R² and R³, when together form a single ring group with the N to which they are bonded, are a heteroaryl ring;
Q is halogen; and
G² is a primary amine precursor.

6. The process of claim 4 further comprising, reacting a compound of Formula 2:

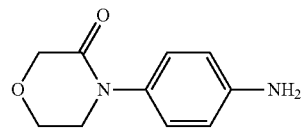

2 with a compound of Formula 8:

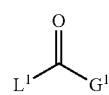

8 thereby forming the compound of Formula 9
wherein
L¹ is a leaving group selected from the group consisting of: halogen, imidazole, ester, C₁-C₄ alkoxy, trihalomethoxy, N-hydroxysuccinimide, p-nitrophenol, N-hydroxyphthalimide, and N-hydroxybenzotriazole;
G¹ is OR¹, NR²R³ or CQ₃;

$R^1$ is alkyl, substituted alkyl, aryl, substituted aryl, arylalkyl or substituted arylalkyl;

$R^2$ and $R^3$ are either (a) two independent groups or (b) together form a single ring group with the N to which they are bonded;

$R^2$ and $R^3$, when independent groups, are independently selected from the group consisting of: H, alkyl, substituted alkyl, aryl, substituted aryl, arylalkyl and substituted arylalkyl;

$R^2$ and $R^3$, when together form a single ring group with the N to which they are bonded, are a heteroaryl ring; and Q is halogen.

7. The process of claim 5 further comprising reacting a compound of Formula 2:

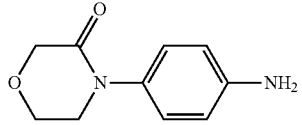

with a compound of Formula 10':

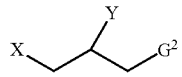

thereby forming the compound of Formula 7'
wherein
X and Y are either i) separate groups or ii) together form a single ring group with the two carbons to which they are bonded; and when: i) X and Y are separate groups, X is a halogen and Y is —OH; or ii) X and Y together form a single ring group with the two carbons to which they are bonded, they are an oxygen atom; and $G^2$ is a primary amine precursor.

8. The process of claim 5 further comprising reacting either:

i) a compound of Formula 4':

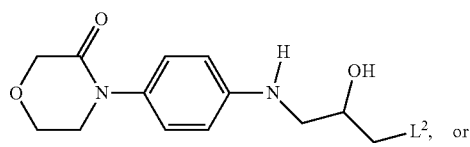

ii) a compound of Formula 6':

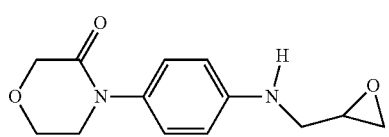

with a compound of Formula 5:

thereby forming the compound of Formula 7'
wherein
$L^2$ is a halogen or sulfonyloxy group;
M is H or a metal selected from the group consisting of Li, Na and K; and
$G^2$ is a primary amine precursor.

9. The process of claim 8 wherein the compound of Formula 4' is reacted with the compound of Formula 5 and further comprising reacting a compound of Formula 2:

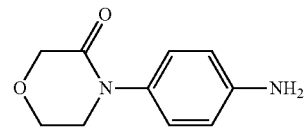

with a compound of Formula 3':

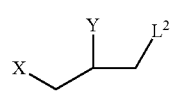

thereby forming the compound of Formula 4'
wherein
X and Y are either i) separate groups or ii) together form a single ring group with the two carbons to which they are bonded; and when: i) X and Y are separate groups, X is a halogen and Y is —OH; or ii) X and Y together form a single ring group with the two carbons to which they are bonded, they are an oxygen atom; and
$L^2$ is a halogen or sulfonyloxy group.

10. The process of claim 8 wherein the compound of Formula 6' is reacted with the compound of Formula 5 and further comprising reacting a compound of Formula 4':

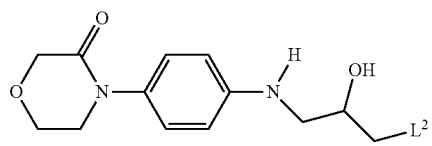

with a sixth base selected from the group consisting of: metal hydroxides, carbonates, phosphates, tertiary amines, aryl amines, and mixtures thereof,
thereby forming the compound of Formula 6'
wherein $L^2$ is a halogen or sulfonyloxy group.

11. The process of claim 1 wherein $G^1$ is $OR^1$ and $G^2$ is an azide or $NR^{2'}R^{3'}$, wherein $R^{2'}$ and $R^{3'}$ are either two independent groups or together form a single ring group with the N to which they are bonded; $R^{2'}$ and $R^{3'}$, when independent groups, are independently selected from the group consisting of: hydrogen and a suitable amine protecting group, provided that both $R^{2'}$ and $R^{3'}$ are not both hydrogen; $R^{2'}$ and $R^{3'}$, when together, form a single ring group with the N to which they are bonded, are a heterocyclic ring, a substituted heterocyclic ring, phthalimide or saccharin.

12. The process of claim 1 wherein $G^1$ is $OR^1$ and $G^2$ is an azide, heterocyclic or substituted heterocyclic ring.

13. The process of claim 12 wherein $R^1$ is an alkyl and $G^2$ is a heterocyclic ring or a substituted heterocyclic ring.

14. The process of claim 3 wherein $G^1$ is $OR^1$ and $G^2$ is an azide, heterocyclic or substituted heterocyclic ring.

15. The process of claim 3 wherein $X^1$ is halogen.

16. The process of claim 5 wherein $G^2$ is an azide, heterocyclic or substituted heterocyclic ring.

17. The process of claim 5 wherein $G^2$ is phthalimide.

18. The process of claim 5 wherein $L^1$ is halogen and $G^1$ is $OR^1$.

19. The process of claim 8 wherein M is a metal and $G^2$ is an azide, heterocyclic or substituted heterocyclic ring.

20. The process of claim 8 wherein M is potassium and $G^2$ is a phthalimide.

* * * * *